United States Patent [19]

Benneche et al.

[11] 4,423,047
[45] Dec. 27, 1983

[54] PYRIMIDINE-2-SULPHIDES AND THEIR S-OXIDES FOR USE IN MEDICINE AND METHODS OF USE THEREFOR, PHARMACEUTICAL COMPOSITIONS CONTAINING THEM, PROCESSES FOR THEIR PREPARATION AND PER SE NOVEL SULPHIDES AND S-OXIDES

[75] Inventors: Tore Benneche; Mikkel J. Gacek; Kjell Undheim, all of Oslo, Norway

[73] Assignee: Nyegaard & Co. A/S, Olso, Norway

[21] Appl. No.: 223,760

[22] Filed: Jan. 9, 1981

[30] Foreign Application Priority Data

Jan. 10, 1980 [GB] United Kingdom ................. 8000802

[51] Int. Cl.³ .................. A61K 31/505; C07D 239/38
[52] U.S. Cl. .............................. 424/251; 260/239 A; 260/239 B; 260/239 BC; 544/295; 544/296; 544/315; 544/316; 544/317; 544/318
[58] Field of Search ............... 544/316, 317, 318, 295, 544/296, 315; 424/251; 260/239 BC, 239 A, 239 B

[56] References Cited

U.S. PATENT DOCUMENTS 2,876,224 3/1959 Grant et al. ..................... 544/316
3,112,316 11/1963 Westphal et al. ................ 544/317
4,248,618 2/1981 Serban et al. ................... 544/318

FOREIGN PATENT DOCUMENTS 1187 3/1979 European Pat. Off. .
15124 9/1980 European Pat. Off. .
2455582 5/1976 Fed. Rep. of Germany .
2820032 11/1978 Fed. Rep. of Germany .
1561290 2/1980 United Kingdom .

OTHER PUBLICATIONS

Budĕšinský et al., Coll. Czech. Chem. Commun., vol. 30, pp. 3895–3901, (1965).

Budĕšinský et al., Coll. Czech. Chem. Commun., vol. 37, pp. 1721–1733, (1972).
Brown et al., J. Chem. Soc., 1971, pp. 250–256.
Krchnak et al., Coll. Czech. Chem. Commun., vol. 40, pp. 1384–1389, (1975).

Primary Examiner—Mary C. Lee
Attorney, Agent, or Firm—Bacon & Thomas

[57] ABSTRACT

Compounds of the formula

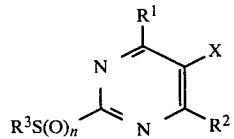

(wherein X represents a halogen atom; n is 0, 1 or 2; $R^1$ and $R^2$, which may be the same or different, each represents a hydrogen atom or a carboxyl, esterified carboxyl, amido or mono- or di-$C_{1-4}$ alkylamido group or a $C_{1-4}$ alkyl group which may if desired carry a carboxyl or esterified carboxyl group; and $R^3$ represents a $C_{1-32}$ saturated or unsaturated, straight or branched, cyclic or acyclic aliphatic group or an araliphatic or heterocyclic substituted aliphatic group, a heterocyclic group or an aryl group which groups may if desired carry one or more substituents selected from halogen atoms and oxo, nitro, hydroxy, etherified hydroxy, esterified hydroxy, primary, secondary or tertiary amino, acylamino etherified mercapto or S=O or —$SO_2$ derivatives thereof and esterified phosphonic acid groups) and, where an acidic or basic group is present, physiologically compatible salts thereof have been found to be of use in combating abnormal cell proliferation. The compounds are prepared inter alia by oxidation of the corresponding sulfide, displacement of a leaving atom or group from the 2-position of the pyrimidine by reaction with a sulfinic acid or by ring closure of the pyrimidine ring.

13 Claims, No Drawings

PYRIMIDINE-2-SULPHIDES AND THEIR S-OXIDES FOR USE IN MEDICINE AND METHODS OF USE THEREFOR, PHARMACEUTICAL COMPOSITIONS CONTAINING THEM, PROCESSES FOR THEIR PREPARATION AND PER SE NOVEL SULPHIDES AND S-OXIDES

The present invention relates to pyrimidine-2-sulphides and their S-oxides having interesting physiological activity and their use as medicaments. More particularly the present invention includes pharmaceutical compositions comprising pyrimidine-2-sulphides and their S-oxides as active ingredients, processes for their preparation and certain of said compounds which are novel per se.

Abnormal cell proliferation is the basic cause of a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

The present invention is based on the discovery that compounds of the formula:

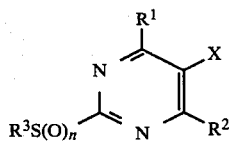

(wherein X represents a halogen atom; n is 0, 1 or 2; $R^1$ and $R^2$, which may be the same or different, each represents a hydrogen atom or a carboxyl, esterified carboxyl, amido or mono- or di-$C_{1-4}$ alkylamido group or a $C_{1-4}$ alkyl group; and $R^3$ represents a $C_{1-32}$ saturated or unsaturated, straight or branched, cyclic or acyclic aliphatic group or an araliphatic or heterocyclic substituted aliphatic group, a heterocyclic group or an aryl group which groups may if desired carry one or more substituents selected from halogen atoms and oxo, nitro, hydroxy, etherified hydroxy, esterified hydroxy, primary, secondary or tertiary amino, acylamino, etherified mercapto or —SO or —$SO_2$ derivatives thereof and esterified phosphonic acid groups) and, where an acidic or basic group is present, the salts thereof possess the ability to inhibit cell proliferation.

Abnormal cell proliferation can be combated by administration of a drug which irreversibly interferes with cell-division. Such drugs are generally only able to attack the cells during a particular phase of the cell cycle, for example the S-phase during which DNA is synthesised. Although the drug cannot distinguish between abnormal and normal cells which are in the phase susceptible to attack, use can be made of the fact that a significant proportion of normal cells, which are of importance in this context (e.g. bone marrow) generally have a shorter cell cycle length than many abnormal cells, such as tumor cells, and hence recover their numbers more rapidly. This effect is further aided by virtue of the fact that, generally a smaller proportion of normal cells would be in cell cycle at the time of drug administration compared with the situation in the abnormal cells, thus providing a larger reservoir from which cells can be recruited for replenishment of normal cells damaged by the drug. The abnormal cell populations are therefore more readily decreased by carefully timed sequential administration of the drug.

Another way in which such a drug can be used to combat abnormal cell proliferation is to administer a preliminary drug which acts to arrest reversibly the cycle of cell division in a particular phase, for example the metaphase, so that when the drug has been eliminated from the system, all the cells resume division synchronously. However, the cell division cycle of the abnormal cells will generally be different from that of the normal cells, and a time can be selected at which the abnormal cells are susceptible to attack by the irreversibly acting drug while the normal cells are in a resistant phase.

The compounds of the present invention inhibit DNA synthesis and are thus particularly useful in combating abnormal cell proliferation.

Thus according to one feature of the present invention there are provided pharmaceutical compositions comprising as active ingredient at least one compound of formula I as hereinbefore defined or, where an acidic or basic group is present, a physiologically compatible salt thereof in association with a pharmaceutical carrier or excipient.

It will be understood that the term "pharmaceutical composition" as used herein, which includes compositions for administration to humans as well as veterinary compositions, is not intended to include mere solutions of the compounds of formula I in non-sterile water or a common organic solvent.

The compositions may be formulated for pharmaceutical administration in any suitable manner. Thus, compositions will normally be in a form suitable for oral, rectal, topical or parenteral administration, such as tablets, coated tablets, capsules, granules, solutions, suppositories, and topical creams, ointments and lotions or sterile solutions in pyrogen-free water for injection or infusion. The compositions will generally be administered at a daily dose level in the range 0.25 to 7.0 g of the compound of the invention; the compositions will conveniently be formulated in dosage units, each dosage unit typically containing from 50 mg to 1.0 g of the compound of the invention, though units containing as much as 5 g may occasionally be suitable.

Conventional carrier and excipient ingredients may be used, such as talc, gum arabic, lactose, starch, magnesium stearate, cocoa butter, animal and vegetable fats, paraffin derivatives, glycols, propellants, and various wetting, dispersing, emulsifying, flavouring and preserving agents.

According to a further feature of the present invention there is provided a method of inhibiting DNA synthesis in the animal cells of a host which comprises administering to said host an effective amount of a compound of formula I as hereinbefore defined or, where an acidic or basic group is present, a physiologically compatible salt thereof.

According to a still further feature of the invention we provide, for use in medicine the compounds of formula I as hereinbefore defined and, where an acidic or basic group is present, physiologically compatible salts thereof, more especially for use in combating abnormal cell proliferation.

Certain of the compounds of formula I have been described generally in Belgian Patent Specification No. 847,234 as intermediates, without any physiological activity being ascribed to them and without any specific compounds being named. Moreover 5-chloro- and 5- bromo-2-methanesulfonyl pyrimidine and the 4-carboxy derivatives thereof and 5-fluoro-2-methanesulfonyl pyrimidine are specifically disclosed in Budesinsky Z. and Vavrina J. Collect. Czech Chem. Commun. 37 (1972) 1721, but, again, no physiological activity is ascribed to these compounds.

Thus according to a further feature of the present invention there are provided novel compounds of formula I as hereinbefore defined wherein X, n, $R^1$, $R^2$ and $R^3$ are as hereinbefore defined, with the proviso that $R^3$ is not an unsubstituted alkyl, aralkyl or aryl group other than a phenyl or benzyl group when $R^1$ and/or $R^2$ is hydrogen or a $C_{1-4}$ alkyl, alkenyl or alkynyl group and X represents a fluorine, chlorine or bromine atom and $R^3$ is other than a methyl group when $R^1$ is a carboxyl group, $R^2$ is a hydrogen atom and X is a chlorine or bromine atom. Thus for example $R^3$ in the novel compounds of the present invention may represent a phenyl or benzyl group or a substituted alkyl, aralkyl or aryl group or a heterocyclic or heterocyclic substituted aliphatic group when X represents a fluorine, chlorine or bromine atom. All the compounds of formula I in which X is iodine are novel compounds.

The terms ued in the above definitions of the compounds of formula I are more particularly discussed below.

The term "aliphatic" includes as preferred groupings $C_{1-8}$, more preferably $C_{1-4}$, alkyl, alkenyl or alkynyl groups, which may carry one or more substituents such as halogen, e.g. chlorine or iodine, oxo, amino, hydroxy, heterocyclic, etherified hydroxy, etherified mercapto, esterified hydroxy or mercapto groups. The term "aliphatic" also includes such radicals which comprise $C_{3-8}$ cyclo-alkyl or -alkenyl groups which groups may, if desired, carry fused rings.

It will be appreciated that when an oxo group is situated on a carbon atom carrying an amino, mono- or di-alkylamino, hydroxy or etherified hydroxy group, then a carbonyl function such as a carbamoyl mono- or di-alkylcarbamoyl, ureido, carboxy or esterified carboxy group will be present. Such carbonyl functions may be substituents on $R^3$ groupings or may be the group $R^3$ itself as in carbamoylthio groupings.

The term "heterocyclic" as used herein preferably relates to groups having 3 to 9, advantageously 5 to 7, ring members and having one or more heteroatoms selected from oxygen, nitrogen or sulfur and optionally carrying a fused ring or carrying one or more hydrocarbon substituents such as aliphatic groups e.g. $C_{1-4}$ alkyl groups, aromatic rings such as phenyl groups or further heterocyclic rings. The ring systems may be saturated or unsaturated, e.g. aromatic. Examples of such groups include thienyl, furyl, 2,4-dihydro-1H-1,4-diazepinyl, epoxy, azetidinone, perhydroazocinyl and pyrimidinyl groups optionally substituted by halogen e.g. chlorine. The term extends inter alia to saccharide residues, i.e. glycosyl groups, for example, furanosyl and pyranosyl derivatives e.g. glucofuranosyl or glucopyranosyl derivatives, including deoxy derivatives thereof the hydroxy groups of which may, if desired, be esterified, as in the 2,3,4;6-tetra-O-acetylglucopyranosyl or 2,3,5-tri-O-benzoyl-β-D-ribofuranosyl group.

The term "aryl" as used herein relates, for example, to aromatic ring systems with up to 10 carbon atoms e.g. phenyl or naphthyl optionally substituted as indicated above, such as a phenyl or p-chlorophenyl group. The term "aryl", it will be understood, also includes within its scope aromatic ring systems substituted by an aliphatic grouping such as an alkyl group e.g. with 1 to 4 carbon atoms e.g. a p-tolyl group, or another aromatic ring such as phenyl, as in the diphenyl group.

Preferably only one of $R^1$ and $R^2$ is other than hydrogen or $C_{1-4}$ alkyl, at least one desirably being hydrogen. It is especially preferred that both of $R^1$ and $R^2$ are hydrogen. Where $R^1$ and/or $R^2$ is esterified carboxyl, this is preferably $C_{1-4}$ alkoxycarbonyl.

The term "araliphatic" as used herein relates, for example, to aralkyl groups with up to 4 carbon atoms in the aliphatic portion, optionally substituted in the aryl ring as indicated above. The aliphatic portion may be unsaturated and may carry one or more substituents e.g. an oxo group.

Examples of such araliphatic groups thus include benzyl, phenethyl, trityl, styryl and phenacyl groups.

$R^3$ in the compounds of formula I as hereinbefore defined may, for example, represent a group or radical which carries one or more etherified hydroxy groups or etherified mercapto or SO or —SO$_2$ derivatives thereof. The etherified hydroxy and mercapto substituents as well as the SO and SO$_2$ derivative substituents are, for example, aliphatic-, araliphatic-, heterocyclic-, or aryl-, —O—, —S— or —SO$_2$— groups (the terms "aliphatic", "araliphatic", "heterocyclic" and "aryl" being as hereinbefore defined), conveniently —O—aryl, —S—aryl, —SO$_2$—aryl, —O—heterocyclic, —S—heterocyclic or —SO$_2$—heterocyclic e.g. phenoxy, pyrimidinyloxy, pyrimidine-2-thio and pyrimidine-2-sulfone groups. It will be appreciated that the above-mentioned substituent groups may themselves be substituted as hereinbefore defined. Thus, for example, substituents may include halogen substituted —O—aryl, —S—aryl, —SO$_2$—aryl, —O—heterocyclic, —S—heterocyclic and —SO$_2$—heterocyclic e.g. p-chlorophenoxy, 5-chloropyrimidin-2-yloxy, 5-chloropyrimidin-2-yl-mercapto and 5-chloropyrimidin-2-yl sulfone groups.

Where $R^3$ carries an esterified hydroxyl or mercapto group, the esterifying groups may be derived from an aliphatic, araliphatic, heterocyclic or aromatic carboxylic acid, for example, a $C_{2-5}$ alkanoic acid such as acetic acid or a $C_{7-11}$ aroic acid such as benzoic acid.

Where $R^3$ contains an esterified carboxyl substituent, or is itself such a substituent (namely a $C_1$ alkyl group carrying both an oxo group and an etherified hydroxyl group) the esterifying group may be an aliphatic, araliphatic, heterocyclic or aryl group as defined above as, for example, in the 2-thienylmethoxycarbonylmethylthio grouping.

Esterified phosphonic acid groups as substituents in $R^3$ include, for example, di($C_{1-8}$alkyl)phosphonate groups e.g. di($C_{1-4}$alkyl)phosphonate groups such as the diethylphosphonate group.

$R^3$ in the compounds of formula I as hereinbefore defined may also, for example, represent a group or radical which may carry one or more primary, secondary or tertiary amino groups or acylamino, e.g. alkanoylamino groups.

Substituents on secondary and tertiary amino groups may, for example, be $C_{1-4}$ alkyl, $C_{6-10}$ aralkyl or aryl or heterocyclic groups having 5 to 10 ring members e.g. as defined above, examples being methyl, ethyl phenyl and tolyl group.

Compounds of formula I containing solubilising groups are of particular interest. Such compounds include for example, polyhydroxy containing groups such as groups derived from carbohydrates, amino acids, hydroxy acids and phosphorus containing organic groups e.g. phosphoric acid derivatives, as well as basic heterocyclic rings such as the 2,4-dihydro-1H-1,4-diazepinyl group.

The radical X in the compounds of formula I may be fluorine, chlorine, bromine, or iodine.

Compounds of formula I wherein n is 1 or 2 are preferred, the sulphones being somewhat more active than the sulphoxides.

Certain of the compounds of formula I may exist in salt form. Where acidic groupings are present in the compounds of formula I salts may be formed with alkali metal or alkaline earth metals e.g. sodium, potassium, magnesium or calcium or ammonium (including substituted ammonium) salts. Compounds according to the invention carrying basic, e.g. hydroxy or amino, groups also in general, possess enhanced water solubility the latter of course forming acid addition salts e.g. with mineral acids such as hydrochloric acid or sulphuric acid or organic acids such as acetic, tartaric or citric acid. However, in general, non-ionic compounds of the invention are preferred. It will be appreciated that the salts of the compounds of formula I for use in pharmaceutical compositions are the physiologically compatible salts. Other salts may however be useful in the preparation of the compounds of formula I and the physiologically compatible salts thereof.

Preferred compounds of the present invention, based on their activity, include compounds of formula I in which $R^3$ represents a $C_{1-3}$ alkyl or alkenyl group which may carry a halogen atom, a monocyclic, carbocyclic or heterocyclic aromatic ring or an optionally substituted pyrimidinyloxy group, for example, a methyl, halomethyl, e.g. chloromethyl or iodomethyl group, a methyl, ethyl or vinyl group carrying an acetyl group or a monocyclic carbocyclic or heterocyclic aromatic 5- or 6-membered ring e.g. a phenyl or thienyl group or a methyl group carrying a 5-halopyrimidin-2-oxy group, e.g. a 5-chloropyrimidin-2-oxy group; or a salt thereof. In such compounds n is preferably 2 and $R^1$ and $R^2$ are preferably hydrogen.

Compounds of the present invention of particular interest in view of their physiological activity also include the following compounds:

2-Methylsulfonyl-5-chloropyrimidine,
2-(Chloromethyl)sulfonyl-5-chloropyrimidine,
2-Styrylsulfonyl-5-chloropyrimidine,
2-Benzylsulfonyl-5-chloropyrimidine,
2-(3-Oxobuten-1-yl)sulfonyl-5-chloropyrimidine,
2-(5-Chloropyrimidine-2-oxymethyl)sulfonyl-5-chloropyrimidine,
2-(Iodomethyl)sulphonyl-5-chloropyrimidine,
2-Benzylsulfonyl-5-bromopyrimidine,
2-Benzylsulfinyl-5-chloropyrimidine, and
2-(2-Thienylmethyl)sulfonyl-5-bromopyrimidine.

It will be appreciated that certain of the compounds of formula I will exist in geometrically or optically active isomeric forms. The present invention extends to cover all of these isomeric forms.

The present invention also relates to the compounds of formula I as hereinbefore defined when used as medicaments and to such use per se.

According to a still further feature of the present invention there is provided a process for the preparation of novel compounds of formula I according to the invention as hereinbefore defined (wherein n is 2) which comprises oxidising a compound of the formula:

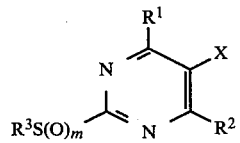

wherein $R^1$, $R^2$, $R^3$ and X are as hereinbefore defined and m is 0 or 1.

The compound of formula I wherein n is 1 is preferably prepared by oxidising a corresponding compound of the formula II (wherein m is O and $R^1$, $R^2$, $R^3$ and X are as hereinbefore defined) to form a compound of formula I wherein n is 1.

The oxidation of the compound of formula II may be effected by any convenient method including the use of (1) a manganese oxidising agent, for example a permanganate preferably potassium permanganate, conveniently in the presence of an acid e.g. acetic acid; (2) the use of chlorine or a hypochlorite e.g. sodium hypochlorite in an aqueous solution of the sulfide or sulfoxide; or (3) the use of a peroxide or peracid oxidising system such as hydrogen peroxide conveniently in the presence of an acid e.g. acetic acid advantageously at ambient temperature, or more preferably, m-chloroperbenzoic acid conveniently at a low temperature e.g. at a temperature from $-30°$ C. to $-5°$ C., or the use of a molybdenum peroxide conveniently in the presence of water and/or hexamethyl-phosphoramide.

In general each oxidation method may be employed to prepare either the sulfone or the sulfoxide, the reaction conditions e.g. reaction time, temperature or excess of reagent being altered depending upon the desired product. Thus if it is desired to prepare the sulfone, longer reaction times, higher temperatures and/or excess of the oxidising agent may for example be used.

It is preferred, however, to effect oxidation to the sulfoxide by for example the use of (1) m-chloroperbenzoic acid conveniently at a low temperature, e.g. at a temperature of from $-30°$ C. to $-5°$ C., to avoid further oxidation to the sulfone; (2) hydrogen peroxide, conveniently in the presence of an acid, e.g. acetic acid, advantageously at a low temperature, e.g. ambient temperature, an excess of the oxidising reagent being avoided in order to reduce sulfone formation; and (3) hydrogen peroxide and selenium dioxide, advantageously under neutral conditions, conveniently in the presence of a solvent, e.g. an alkanol such as methanol. These processes are preferred for sulfoxide production because the oxidation reaction may be terminated more readily at the sulfoxide stage. The course of the oxidation may, for example, be monitored using chromatographic techniques.

Where it is desired to prepare the sulfone the oxidation may, for example, be effected (1) by the use of m-chloroperbenzoic acid, conveniently in the presence of a solvent e.g. dichloromethane, the oxidation being, for example, effected at a higher temperature than for sulfoxide formation; (2) by the use of hydrogen peroxide conveniently in the presence of an acid, e.g. acetic acid, the oxidation being, for example, effected in the presence of an excess of the oxidising agent and/or at a higher temperature than for sulfoxide formation (3) the use of chlorine, for example in aqueous solution, this method being preferred for sulfone formation especially when the sulfide (compound of formula II) is less readily oxidizable; (4) the use of a manganese oxidising agent, for example, potassium permanganate, conveniently in the presence of an acid, e.g. acetic acid, this method also being preferred for formation of the sulfone, by virtue of the higher yields which may be obtained in comparison with milder oxidising agents; and (5) the use of molybdenum peroxide, conveniently in the presence of water and/or hexamethylphosphoramide, this method also being preferred for sulfone formation.

A compound of formula I in which n is O is conveniently first prepared by condensing a compound of the formula

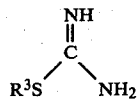   III (wherein $R^3$ is as hereinbefore defined) or an acid addition salt thereof with a compound of the formula

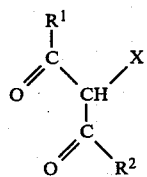   IV (wherein $R^1$, $R^2$ and X are as hereinbefore defined) or a functional derivative thereof such as an enol, enol ether, enol thioether, enamine or imine derivative whereby a compound of formula I in which n is 0 is obtained.

The condensation is conveniently effected under acid conditions, preferably in a solvent such as an alcohol e.g. ethanol. Where $R^1$ and $R^2$ each represent hydrogen the reaction is advantageously effected at ambient temperature. A functional derivative of a compound of formula IV may for example be derived by reaction of both carbonyl groups of the compound of formula IV with a dialkylamine such as dimethylamine; one of the imine groups so produced may rearrange in such a compound to the enamine form.

The compound of formula I in which n is 0 may also be prepared, for example, by reaction of a compound of the formula

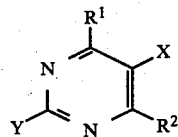   V (wherein $R^1$, $R^2$ and X are as hereinbefore defined and Y represents a leaving atom or group) with a thiol of the formula $R^3SH$ or a thiolate of the formula $[R^3S]_n {}^{\ominus} M^{n\oplus}$   VI (wherein $R^3$ is as hereinbefore defined, M represents the stabilising cation and n represents the charge on the cation) whereby a compound of formula I in which n is 0 is obtained.

The reaction of the compound of formula V with the compound of formula VI is conveniently effected by the use of a compound of formula V in which Y represents a halogen atom e.g. a chlorine or bromine atom. The reaction is a nucleophilic substitution reaction, the nucleophile being in the form $R^3S^-$ and thus where the compound of formula VI is used in the form of a thiol, the reaction is preferably effected in the presence of a base sufficiently strong to remove the thiol proton to give the aforementioned nucleophile. Preferred bases include alkoxides, for example alkali metal and alkaline earth metal alkoxides such as sodium or potassium alkoxides e.g. ethoxides. The reaction is conveniently effected at an elevated temperature preferably at the reflux temperature of the reaction mixture.

The compound of formula II may also be prepared, for example, by reacting a compound of the formula

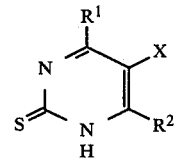   VII (wherein $R^1$ $R^2$ and X are as hereinbefore defined) with a reagent serving to alkylate the sulphur atom to add a group $R^3$ thereto, for example an alcohol $R^3OH$ or an alkylating derivative thereof.

Such an alkylating derivative may be of the formula:

$R^3Y$   VIII (wherein $R^3$ and Y are as hereinbefore defined). The reaction is preferably effected in the presence of a base or by phase-transfer catalysis, for example by the use of a triethylbenzylammonium compound, e.g. the chloride, hereinafter referred to as TEBA. Moreover the reaction is preferably effected using a compound of formula VIII in which Y represents a halogen atom e.g. a chlorine or bromine atom. The reaction is conveniently effected at ambient temperature.

The alkylating agent reacted with the compound of formula VII may also be an epoxide or azirane, the product thus formed being a 2'-hydroxy or 2'-aminoalkyl thio derivative. However, where the epoxide carries a leaving group such as a halogen atom, adjacent to the epoxy group as in epichlorohydrin, the leaving group may be eliminated subequently, together with the hydrogen atom of the hydroxyl group, to provide a further epoxide grouping.

An alternative alkylating derivative is an acetal of the alcohol $R^3OH$, for example an acetal with a dialkylformamide such as dimethylformamide.

The reaction of the alcohol $R^3OH$ with the thione of formula VII requires the presence of a condensation catalyst, for example a di-t-alkyl acetal of a dialkylformamide. The alkyl groups present in the dialkylformamide may have 1-5 carbon atoms, methyl being preferred. The t-alkyl groups are preferably neopentyl groups. The reaction is generally effected at elevated temperature.

Where the compound of formula VII is reacted with a difunctional alkylating agent such as diiodeomethane, dimeric compounds of formula II are formed in which effectively $R^3$ is an alkyl group carrying 5-halo-pyrimindine-2-thio substituent, i.e. an etherified mercapto group. It is found that oxidation of such a dimer by the methods described above can selectively convert only one of the S-atoms to SO.

We have also found that the above dimeric compounds may be formed by heating a compound of formula II in which $R^3$ is a haloalkyl group, e.g. a chloromethyl group, with a base such as morpholine.

Such compounds of formula I in which n is 0 and $R^3$ is an alkyl group carrying a chlorine atom on the α-carbon atom, e.g. chloromethyl, may be prepared by reaction of the corresponding alkyl derivative having an α-hydrogen atom with a chlorinating agent, e.g. sulphuryl chloride for example at elevated temperature. Such haloalkyl derivatives may serve as indicated above as precursors for the preparation of Wittig reagents. Where a corresponding compound is required in which $R^3$ is an alkyl group carrying a halogen atom other than chlorine, halogen exchange may be effected e.g. by reaction with an iodide or fluoride.

According to a further feature of the present invention there is provided a process for the preparation of compounds of formula I as hereinbefore defined (wherein n is 0, 1 or 2 and $R^3$ represents a vinyl group of the formula:

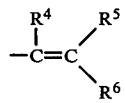

(wherein $R^4$, $R^5$ and $R^6$, which may be the same or different, each represent a hydrogen atom or a $C_{1-8}$ alkyl group, an aralkyl group, a heterocyclic alkyl group, an aryl group or a heterocyclic group which groups may optionally be substituted as hereinbefore defined), which process comprises the reaction of a compound of the formula:

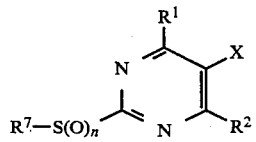

IX (wherein $R^7$ represents the group $-CHR^4-P(O)R^8R^9$ or

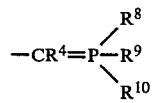

in which $R^4$ is as herein described and $R^8$, $R^9$ and $R^{10}$, which may be the same or different, each represents an aryl or alkoxy group) with a compound of the formula:

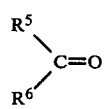

(wherein $R^5$ and $R^6$ are as herein defined) whereby the desired vinyl derivative is obtained.

The compound of formula IX is conveniently first prepared by reaction of a compound of formula I in which $R^3$ represents the group $-CHR^4Y-$ (wherein Y and $R^4$ are as hereinbefore defined) with a phosphine or phosphite for example a triarylphosphine e.g. triphenylphosphine or a trialkylphosphite e.g. triethylphosphite.

The vinylation reaction is conveniently effected under the conditions of a Wittig reaction or preferably a Horner-Wittig reaction.

Vinylation may also be effected by reaction of a compound of formula VII (wherein $R^1$ and $R^2$ have the above meanings) with an ethynyl compound of the formula $R^4-C\equiv C-R^7$ (wherein $R^4$ has the above meaning and $R^7$ is preferably an acyl group e.g. a lower alkanoyl ($C_{1-8}$) group, such as an acetyl group or a carbonyl group or derivative thereof such as an amide or ester group); $R^4$ is preferably hydrogen. The reaction may be effected in an inert solvent e.g. a halohydrocarbon such as chloroform.

Compounds of formula I as hereinbefore defined wherein $R^3$ represents a propargyl group may be prepared by the processes described above. Depending upon the reaction conditions however the propargyl group may isomerize to yield the corresponding propadienyl compound. Thus the reaction product may be a propargyl compound, a propadienyl compound or a mixture of the isomers. Where, for example the propargyl sulfide of formula I is oxidised using p-chloroperbenzoic acid the sulfide may be oxidised to the sulfone, the propargyl group being isomerised under the conditions of the oxidation to give the propadienyl isomer in high yield. On the other hand, when selenium dioxide and hydrogen peroxide are used, the product is the propargylsulphinyl derivative.

The compounds of formula I in which n=2 may also be formed directly from compounds of the formula V (wherein $R^1$, $R^2$, X and Y have the above meanings) by reaction with a sulphinic acid of the formula $R^3SO_2H$ or a salt thereof. Where the acid is used the reaction should be effected in the presence of a base. The salt of the sulfinic acid may for example, be an alkali metal or alkaline earth metal or a tertiary organic base salt. The reaction may be effected in a polar solvent such as an alkanol e.g. methanol. A quaternary ammonium salt such as triethylbenzylammonium chloride may usefully be present as a phase transfer catalyst for the salt, usefully in the presence of lithium chloride.

The reaction will now be more particularly described in the following Examples, which are by way of illustration only. Many of the starting compounds have been prepared according to prior art publications and reference numbers are given when appropriate as follows.

EXAMPLE 1

2-Phenylthio-5-chloropyrimidine

A solution of thiophenol (60 mmol) in 0.43 M sodium ethoxide (150 ml) and a solution of 2,5-dichloropyrimidine (60 mmol) in absolute ethanol (90 ml) were mixed and heated under reflux for 2 h. The cold mixture was then filtered, the filtrate evaporated, the residual material dissolved in chloroform (150 ml), the chloroform solution washed with 2 M NaOH (2×15 ml) and water (15 ml) and the dried (MgSO4) solution evaporated leaving an oily material which crystallized in the cold; yield 70%, m.p. 47° C. (ligroin). $^1$H NMR (CDCl$_3$): δ7.4(Ph), 8.33 (H-4, H-6).

EXAMPLE 2

2-Benzylthio-5-chloropyrimidine

Method A

A solution of 5-chloropyrimidine-2-thione (4.6 mmol) and 2 M NaOH (7 ml) was mixed with a solution of benzyl bromide (6.9 mmol) and triethylbenzylammonium chloride (TEBA; 4.6 mmol) in dichloromethane (20 ml). The two-phase system was vigorously stirred at room temperature for 16 h, the layers separated, the aqueous solution extracted with dichloromethane, the dichloromethane solutions combined and washed with water, and the dried ($MgSO_4$) solution evaporated; yield 46%. The crude product was sufficiently pure for the successive oxidation. $^1$H NMR ($CDCl_3$): $\delta$4.45 ($CH_2$), 7.28 (Ph), 8.41 (H-4, H-6).

Method B

A solution of 1,3-bis-N,N-dimethylamino-2-chlorotrimethinium perchlorate (38.3 mmol) and benzylisothiouronium chloride (40.7 mmol) was prepared in methanol (100 ml) and tert-BuOK (40.7 mmol) added portionwise. The reaction mixture was stirred at room temperature for 30 min after the addition was completed, when additional tert-BuOK (38.3 mmol) was added and the mixture heated under reflux for 2.5 h. The precipitate was removed, the solvent distilled from the filtrate, water (20 ml) added to the residue, the aqueous solution extracted with ether, the ether solution dried ($MgSO_4$), and HCl gas passed through the solution at 0° C. The precipitated salt is dissociated when dried in vacuo and the HCl is lost; yield 43%, m.p. 57° C. (dil. MeOH). $^1$H NMR ($CDCl_3$): $\delta$4.33 ($CH_2$), 7.26 (Ph), 8.40 (H-4, H-6).

EXAMPLE 3

2-Phenylthio-5-bromopyrimidine

The title compound was prepared from 2-chloro-5-bromo-pyrimidine and thiophenol as described in Example 1; yield: 90% of a non-crystalline product which was pure enough for the successive oxidation. MS m/e: 267 (M, 100%). $^1$H NMR ($CDCl_3$): $\delta$7.4 (Ph), 8.50 (H-4, H-6).

EXAMPLE 4

2-Allylthio-5-chloropyrimidine

Method A 1,3-Bis-N,N-dimethylamino-2-chlorotrimethinium perchlorate (31 mmol) and 2-allylisothiouronium bromide (35 mmol) were dissolved in methanol and methanolic 1.67 M sodium methoxide (35 mmol) added. The mixture was stirred at room temperature for 30 min before an additional 19 ml of the sodium methoxide solution (31 mmol) were added. The mixture was then heated under reflux for 2.5 h, the solvent distilled off, water (100 ml) added to the residue, the mixture extracted with chloroform, the dried ($MgSO_4$) chloroform solution evaporated, and the residue distilled; yield 86%, b.p. 62°–64° C./0.1 mmHg. ($^1$H NMR ($CDCl_3$): $\delta$3.76 (2H—$CH_2$), 5.0–6.4 (3H-vinyl), 8.40 (H-4, H-6).

Method B

5-Chloropyrimidine-2-thione (8 mmol) and N,N-dimethylformamide diallyl acetal (8 ml) were heated together in acetonitrile (40 ml) at 70° C. for 90 min. The solvent was then distilled off, the residue dissolved in ether (50 ml), the solution extracted with 2 M NaOH (2×50 ml), the ether solution washed and dried ($MgSO_4$), the ether evaporated and the residue distilled; yield 74%, b.p. 62°–63°/0.1 mmHg.

EXAMPLE 5

2-Benzylthio-5-chloropyrimidine

5-Chloropyrimidine-2-thione (8 mmol) and N,N-dimethylformamide dibenzyl acetal (8 mmol) were heated together in acetonitrile (40 ml) at 70° C. for 90 min. The solvent was then distilled off, the residue dissolved in ether (50 ml), the ether solution extracted with 2 M NaOH (2×5 ml), washed with water (5 ml) and dried ($MgSO_4$) and gaseous HCl passed into the solution. The title compound was precipitated as the HCl-salt; yield 80%. (Physical data: as detailed in Example 2).

EXAMPLE 6

Bis(5-chloropyrimidin-2-ylthio)methane

Method I

Methanolic 2 M sodium methoxide (9 mmol) and diiodomethane (20 mmol) were added to a solution of 5-chloropyrimidine-2-thione (9 mmol) in methanol (20 ml) and the mixture stirred at room temperature for 2 h. The solid precipitate was collected, washed well with water and recrystallized from ethanol; yield 88%, m.p. 162° C. ($^1$H NMR ($CDCl_3$): $\delta$4.83 ($CH_2$), 8.50 (4H-4,6, s).

Method II

2-Chloromethylthio-5-chloropyrimidine (0.5 mmol) and morpholine (1 ml) were heated together in benzene (5 ml) overnight. A little precipitate was removed by filtration and the filtrate evaporated. The residue was washed with water and recrystallized from ethanol; yield 92%, physical data as above.

EXAMPLE 7

2-(Chloromethyl)thio-5-chloropyrimidine

2-Methylthio-5-chloropyrimidine (75 mmol) and sulfuryl chloride (104 mmol) were heated together in refluxing dichloromethane (100 ml) for 3 h. Evaporation of the mixture left a solid which was recrystallized from ethanol; yield 82%, m.p. 78° C. $^1$H NMR ($CDCl_3$): 5.20 ($SCH_2$), 8.54 (H-4, H-6).

EXAMPLE 8

2-(Iodomethyl)thio-5-chloropyrimidine

Sodium iodide (30 mmol) was added to a solution of 2-chloromethylthio-5-chloropyrimidine (6.7 mmol) in acetone (30 ml) and the mixture heated under reflux for 4 h. The precipitated sodium chloride was removed by filtration, the filtrate evaporated to dryness, the residue triturated with water and recrystallized from ethanol; yield 86%, m.p. 67° C. $^1$H NMR ($CDCl_3$): $\delta$4.82 ($SCH_2$), 8.67 (H-4, H-6).

EXAMPLE 9

2-Methylthio-4-methoxycarbonyl-5-chloropyrimidine

A solution of 2-methylthio-4-carboxy-5-chloropyrimidine (31 mmol) in thionyl chloride (50 ml) was heated under reflux for 60 min. Excess thionyl chloride was distilled off, the residual material dissolved in methanol (70 ml), the solution heated under reflux for 30 min, excess methanol distilled off, the residue dissolved in chloroform, the chloroform solution washed with sodium bicarbonate and water, and the dried (MgSO$_4$) solution evaporated and the residue distilled; yield 78%, b.p. 108°–110° C./0.15 mmHg. $^1$H NMR (CDCl$_3$): δ2.56 (SMe), 4.00 (OMe), 8.63 (H-6).

EXAMPLE 10

2-Methylthio-4-N,N-diethylaminocarbonyl-5-bromopyrimidine

2-Methylthio-4-carboxy-5-bromopyrimidine (11 mmol) in thionyl chloride (25 ml) was heated under reflux for 70 min. Excess thionyl chloride was distilled off, the residual material dissolved in toluene and a solution of diethylamine (22 mmol) in toluene (20 ml) added dropwise with vigorous stirring. The mixture was heated at 90° C. for 45 min., the solvent evaporated, the residue extracted with chloroform (100 ml), the chloroform solution washed (3×10 ml) and dried (MgSO$_4$), and the solution filtered through an alumina column (30 g, activity III). Evaporation of the chloroform eluate left an oily material which slowly crystallized; yield 74%, m.p. 81° C. (hexane). $^1$H NMR (CDCl$_3$): 1.21 and 3.16/3.58 (NEt$_2$) 2.55 (SMe), 8.63 (H-6).

EXAMPLE 11

Diethyl (5-chloropyrimidine-2-thio)methanephosphonate 2-(Chloromethyl)thio-5-chloropyrimidine (20 mmol) and triethyl phosphite (15 ml) were heated together under reflux for 24 h. The reaction mixture was then evaporated to dryness at reduced pressure and the residue purified by thick-layer chromatography; yield of crude product 3.39, m.p. ca 30° C. The product was used in the successive step without further purification. $^1$H NMR (CDCl$_3$): δ1.29 and 4.12 (OEt), 3.54 (2H—CH$_2$, J$_{HP}$ 14 Hz), 8.44 (H-4, H-6). MS [70 eV, m/e (% rel. int.)]: 296 (24, M), 160 (100).

EXAMPLE 12

2-(3-Oxobuten-1-yl)thio-5-chloropyrimidine

3-Butyn-2-one (5 mmol) in chloroform (25 ml) was added dropwise over 10 min at room temperature to a stirred suspension of 5-chloropyrimidine-2-thione (4.5 mmol) in chloroform (25 ml). The mixture was stirred for an additional 10 min before the solvent was evaporated. The residue was crystallized from methanol; yield 72%, m.p. 89° C. $^1$H NMR (CDCl$_3$): δ2.20 (Me-(Z)), 2.23 (Me-(E)), 6.52 (Hα, d, J 18 Hz (E)), 6.58 (Hα, d, J 10 Hz (Z)), 8.43 (Hβ, d, J 10 Hz (Z)), 8.57 (Hβ, d, J 18 Hz (E)), 8.62 (H-4, H-6); (E)/(Z)=1:1. IR (KBr): 1660 cm$^{-1}$ (CO).

EXAMPLE 13

2-(4-Chlorophenoxymethyl)thio-5-chloropyrimidine

A mixture of p-chlorophenoxymethyl chloride (6 mmol) and the potassium salt of 5-chloropyrimidine-2-thione (5 mmol) in 1,2-dimethoxyethane (25 ml) was stirred at room temperature for 10 h, the solvent distilled off at reduced pressure, the residue extracted with chloroform (70 ml), the chloroform (70 ml), the chloroform solution washed with 1 M NaOH (2×10 ml) and water (10 ml), and the dried (MgSO$_4$) solution evaporated. The residual sulfide was recrystallized from iPrOH; yield 70%, m.p. 120° C. $^1$H NMR (DMSO-d$_6$): δ5.90 (SCH$_2$), 6.98 and 7.31 (Ph), 8.78 (H-4, H-6).

EXAMPLE 14

2-(2-Hydroxy-3-chloropropyl)thio-5-chloropyrimidine

A mixture of 5-chloropyrimidine-2-thione (14 mmol) and triethylamine (14 mmol) was stirred together in dichloromethane (30 ml) for 5 min before epichlorohydrin (15 mmol) was added. The mixture was stirred at room temperature for 3 h, the solvent evaporated, the residue triturated with water, the insoluble material extracted with chloroform, the dried (MgSO$_4$) chloroform solution evaporated and the residue crystallized from chloroform:pet. ether; yield 30%, m.p. 99° C. $^1$H NMR (acetone-d$_6$): δ3.3–3.8 (2CH$_2$, m) 3.9–4.4 (CH, m), 4.6–4.7 (OH), 8.59 (H-4, H-6).

EXAMPLE 15

2-Propargylthio-5-chloropyrimidine

A mixture of 5-chloropyrimidine-2-thione (5 mmol) and triethylamine (5 mmol) was stirred together in dichloromethane (40 ml) for 5 min before propargyl bromide (6 mmol) was added. The mixture was stirred at room temperature for 1 h before the solvent was evaporated. The residue was triturated with water (20 ml), and the solid recrystallized from methanol; yield 87%, m.p. 66° C. $^1$H NMR (CDCl$_3$): δ2.16 (HC≡, t, J 2 Hz), 3.88 (CH$_2$, d, J 2 Hz), 8.80 (H-4, H-6). IR (KBr): 3300 Cm$^{-1}$ (HC≡).

EXAMPLE 16

2-(2,3,4,6-Tetraacetylglucopyranosyl)thio-5-chloropyrimidine

A mixture of 5-chloropyrimidine-2-thione (10 mmol) and triethylamine (10 mmol) were stirred together in benzene (35 ml) for 30 min before a solution of tetraacetyl-1-bromoglucose (10 mmol) in benzene (15 ml) was added. The mixture was stirred at room temperature for 4 h, the solid removed and washed with chloroform, the combined chloroform washings and the benzene solution evaporated, the residue triturated with water (20 ml), and the solid crystallized from MeOH; yield 48%, m.p. 172° C. $^1$H NMR (CDCl$_3$): δ2.03 (Ac), 3.8–5.8 (glucose), 8.50 (H-4, H-6).

EXAMPLE 17

2-Phenacylthio-5-bromopyrimidine

5-Bromopyrimidine-2-thione (10.5 mmol) was added to a solution of triethylamine (11.6 mmol) in EtOH (130 ml) and the mixture stirred for 15 min before addition of phenacyl bromide (10.5 mmol). The reaction mixture was stirred for 1 h before the solvent was removed at reduced pressure, the residue extracted with chloroform and the chloroform solution chromatographed on alumina (100 g, activity I); yield 71%, m.p. 107°–109° C. (iPrOH). $^1$H NMR (CDCl$_3$): δ4.60 (CH$_2$), 7.5–8.0 (Ph), 8.46 (H-4, H-6).

EXAMPLE 18

2-(Carbamoylmethyl)thio-4,6-dimethyl-5-bromopyrimidine (a) 4,6-dimethyl-5-bromopyrimidine-2-thione.HCl A solution of 2-chloro-4,6-dimethyl-5-bromopyrimidine (21.7 mmol) and thiourea (21.8 mmol) in ethanol (100 ml) was heated under reflux for 5 h. The solvent was distilled off, the residue extracted with 1 M NaOH (60 ml) by heating for 60 min, the mixture filtered, and the pH of the cold filtrate brought to ca. 3 by means of HCl when the thiolactam was precipitated; yield 60%, m.p. 270° C. (decomp.) (aq EtOH). $^1$H NMR (TFA): $\delta$2.83 (Me).

(b) 2-(carbamoylmethyl)thio-4,6-dimethyl-5-bromopyrimidine 4,6-Dimethyl-5-bromopyrimidine-2-thione HCl salt (5 mmol) was added to ethanolic (60 ml) KOH (11.4 mmol), the solution stirred for 10 min at room temperature, iodoacetamide (5.7 mmol) added, the stirring continued for 20 min at room temperature and for 100 min at 70° C. (pH 8). The warm reaction mixture was filtered, the filtrate evaporated, the residue extracted with chloroform (150 ml), the chloroform solution washed and the dried (MgSO$_4$) solution evaporated to leave the sulfide; yield 72%, m.p. 175°–177° C. (iPrOH). $^1$H NMR (DMSO-d$_6$): $\delta$2.50 (Me), 3.80 (SCH$_2$).

EXAMPLE 19

2-(2-Thienyl)thio-5-chloropyrimidine 2,5-Dichloropyrimidine (11.3 mmol) was added to a solution of thiophene-2-thiol (12.3 mmol) in ethanolic (50 ml) 0.246 M NaOEt. The reaction mixture was stirred at room temperature for 15 min and heated under reflux for 2 h. The solvent was then evaporated, the residue extracted with chloroform, the chloroform solution washed with 2 M NaOH and the dried (MgSO$_4$) solution evaporated to leave the sulfide; yield 89%, m.p. 65° C. (pet. ether b.p. 100° C.). 1 H NMR (CDCl$_3$); $\delta$7.03, 7.26, 7.53 (thiophene), 8.40 (H-4, H-6).

EXAMPLE 20

2-(2-Thienylmethylthio)-5-bromopyrimidine

2-Bromomethylthiophene (15.2 mmol) was added to the potassium salt of 5-bromopyrimidin-2-one (12.6 mmol) in 1,2-dimethoxyethane (50 ml) and the mixture stirred at room temperature for 3 h. The solvent was then removed at reduced pressure, the residue extracted with chloroform (70 ml), the chloroform solution washed with 1 M NaOH (20 ml), washed with water (2×10 ml), and the dried (MgSO$_4$) solution evaporated to yield the sulfide; yield 77%, m.p. 87° C. (iPrOH). $^1$H NMR (CDCl$_3$): $\delta$4.50 (CH$_2$), 6.90 (H-3', H-4'), 7.13 (H-5'), 8.50 (H-4, H-6).

EXAMPLE 21

2-Benzylthio-5-bromopyrimidine

Benzyl thiol (22 mmol) was added to 0.146 M ethanolic NaOEt (150 ml) at room temperature followed by 2-chloro-5-bromopyrimidine (20 mmol). The mixture was stirred at room temperature for 70 min, heated under reflux for 40 min, the solvent evaporated off at reduced pressure, the residue extracted with chloroform (100 ml), the chloroform solution washed with 2 M NaOH, and the dried (MgSO$_4$) solution evaporated; yield 81%, m.p. 68°–69° C. (dil. MeOH). $^1$H NMR (CDCl$_3$): $\delta$4.36 (CH$_2$), 7.26 (Ph), 8.50. (H-4, H-6).

EXAMPLE 22

2-Benzylthio-4,6-dimethyl-5-bromopyrimidine

2-Chloro-4,6-dimethyl-5-bromopyrimidine (10 mmol) was added to a solution of benzylthiol (11 mmol) and 0.138 M NaOEt in ethanol (80 ml). The mixture was stirred at room temperature for 70 min and then heated under reflux for 40 min. The solvent was then distilled off, the residue extracted with chloroform (50 ml), the chloroform solution washed with 2 M NaOH and the dried (MgSO$_4$) solution evaporated to leave the sulfide which was purified by distillation; yield 94%, b.p. 232°–234° C./15 mmHg. $^1$H NMR (Cl$_3$CF): $\delta$2.50 (Me-4, Me-6), 4.26 (CH$_2$), 7.20 (Ph).

EXAMPLE 23

2-(4-Chlorophenoxymethyl)thio-5-chloropyrimidine 2-(Iodomethyl)thio-5-chloropyrimidine was added to a solution of p-chlorophenol (5.5 mmol) and 0.138 M NaOEt in ethanol (40 ml) and the mixture stirred at room temperature overnight. The solvent was distilled off and the mixture worked up as above; yield 64%.

EXAMPLE 24

2-(5-Chloropyrimidin-2-oxymethyl)thio-5-chloropyrimidine and 2-(5-Chloropyrimidin-2-one-1-ylmethyl)thio-5-chloropyrimidine 2-(Iodomethyl)thio-5-chloropyrimidine (15.6 mmol) in DMF (20 ml) was added to the potassium salt of 5-chloropyrimidin-2-one (15.0 mmol) in DMF (60 ml). The mixture was stirred at room temperature for 8 h before the solvent was distilled off. The residue was triturated with water and the insoluble N- and O-alkylated isomers separated by fractional crystallization from acetone; 2-(5-chloropyrimidin-2-oxymethyl) thio-5-chloropyrimidine was the more soluble isomer; yield 36%, m.p. 128° C. (MeOH). $^1$H NMR (CDCl$_3$): $\delta$6.15 (CH$_2$), 8.48 (2H in pyrimidine), 8.51 (2H in pyrimidine).

The less soluble isomer in acetone solution was 2-(5-chloropyrimidin-2-one-1-ylmethyl)thio-5-chloropyrimidine; yield 64%, m.p. 210° C. (acetone). (Found: C 37.59; H 2.07. Calc. for C$_9$H$_6$Cl$_2$N$_4$OS: C 37.38, H 2.10). $^1$H NMR (CDCl$_3$): $\delta$5.56 (CH$_2$—), 8.29 and 8.57 (H-4, H-6, J 3 Hz), 8.62 (H'-H, H'-6). IR (KBr): 1670 (CO) MS (70 eV; m/e (% rel. int)); 288 (20, M) 159 (23), 149 (40), 147 (100), 143 (73).

EXAMPLE 25

2-Propargylthio-5-chloropyrimidine and 2-(1,2-propadienyl)thio-5-chloropyrimidine (a) S-propargylisothiouronium bromide and S-(1,2-propadienyl)isothiouronium bromide Thiourea and propargyl bromide are heated in ethanol as described for the synthesis of the S-propargylisothiouronium bromide (see Salo, K. *Chem Abst* 51 (1957) 17760d) gave instead a mixture of the isomeric title compounds, ratio 1:1. $^1$H NMR (D$_2$O): $\delta$2.90 (S—CH$_2$C≡CH, t, J 2 Hz) and 4.05 (S—CH$_2$C≡CH, d, J 2 Hz), 5.35 (S—CH=C=CH$_2$, d, J, 6 Hz) and 6.08 (S—CH=C=CH$_2$, t, J 6 Hz).

(b) 2-Propargylthio-5-chloropyrimidine and 2-(1,2-propadienyl)thio-5-chloropyrimidine Methanolic sodium methoxide (84 mmol) was added to a solution of 1,3-bis-N,N-dimethylamino-2-chlorotrimethinium perchlorate (40 mmol) and the 1:1 isothiouronium bromides (44 mmol) in methanol (100 ml) and the mixture heated under reflux for 30 min. The solvent was then distilled off, the residue triturated with water and dried. The spectra showed the product to be a mixture of the title compounds, ratio 3:1 ($^1$H NMR); yield 48%.

EXAMPLE 26

2-(2,3-Epoxypropyl)thio-5-chloropyrimidine

A mixture of 5-chloropyrimidine-2-thione (6.9 mmol) and potassium tert-butoxide (6.9 mmol) was stirred together in anhydrous DMF (40 ml) for 5 min before epiiodohydrin (6.9 mmol) was added. The mixture was stirred at 80° C. for 7 h while small portions of potassium tert-butoxide were added from time to time to maintain a strong basic solution. The solvent was then removed at reduced pressure, the residue triturated with water (50 ml), the insoluble material extracted with chloroform and the dried (MgSO$_4$) chloroform solution evaporated leaving the oily sulfide, yield 29%. This material was chromatographically homogenous and was identified by its spectroscopic properties. $^1$H NMR (CDCl$_3$): δ2.6–3.4 (5H, m), 8.50 (H-4, H-6).

EXAMPLE 27

2-(5-nitro-2-thienyl)thio-5-chloropyrimidine

A mixture of 5-chloropyrimidine-2-thione (7.5 mmol), triethylamine (9 mmol) and 2-bromo-5-nitrothiophene (9 mmol) in dichloromethane (50 ml) was stirred at room temperature for 2 days. The resultant solution was then diluted with dichloromethane (50 ml), the solution shaken with 1 M NaOH (2×10 ml) and subsequently with water (10 ml), the dried (MgSO$_4$) solution evaporated and the solid residue recrystallized from pet. ether; yield 63%, m.p. 141°–143° C. $^1$H NMR (CDCl$_3$): δ7.16 and 7.83 (H-3$^1$, H-4$^1$), 8.53 (H-4, H-6).

EXAMPLE 28

2-[N-(2-Tolyl)carbomoylmethyl]thio-4,6-dimethyl-5-bromopyrimidine (a) N-(Iodoacetyl)-2-toluidine A mixture of N-(Bromoacetyl)-2-toluidine (0.16 mmol) and KI (0.32 mmol) in methanol (270 ml) was heated under reflux for 2½ hours. The cold reaction mixture was poured into water (2 l) and the precipitated iodide dried; yield 82%, m.p. 145°–146° C. (MeOH). $^1$H NMR (TFA): δ1.79 (Me), 3.61 (CH$_2$), 6.8 (Ph).

(b) 2-[N-(2-Tolyl)carbamoylmethyl)thio-4,6-dimethyl-5-bromopyrimidine.

N-(Iodoacetyl)-2-toluidine (11.4 mmol) was added to a solution prepared from 4,6-dimethyl-5-bromopyrimidine-2-thione. HCl (10 mmol) and KOH (22.8 mmol) in ethanol (140 ml). The resultant mixture was stirred at room temperature for 20 min and subsequently at 70° C. for 3 hours (pH 8). The warm reaction mixture was then filtered, the filtrate evaporated the residue extracted with chloroform (200 ml), the chloroform solution shaken with water and the dried (MgSO$_4$) solution evaporated; yield 80%, m.p. 168° C. (MeOH).

EXAMPLE 29

2-Phenylthio-5-fluoropyrimidine

A solution of 2-chloro-5-fluoropyrimidine (10 mmol) in ethanol (15 ml) was added dropwise over 5 min to a solution prepared from thiophenol (10 mmol) and 0.43 M NaOEt in ethanol (25 ml). Subsequently the mixture was heated to boiling and refluxed for 2 hours, filtered hot, the filtrate evaporated, the residue extracted with chloroform (50 ml), the chloroform solution shaken with 2 M NaOH (2×10 ml), then shaken with water (10 ml) and the solution evaporated; yield 69%. $^1$H NHR (CDCl$_3$): δ7.4 (Pyr), 8.23 (H-4, H-6).

EXAMPLE 30

2-(4-Azetidin-2-one)thio-5-chloropyrimidine

5-Chloropyrimidine-2-thione (3 mmol) was added to a solution of potassium tert-butoxide (3 mmol) in DMF (10 ml) and the mixture stirred for 10 min before a solution of 4-acetoxyazetidin-2-one (3 mmol) in DMF (10 ml) was added. The resultant solution was stirred at room temperature for 36 hours, the solvent removed at reduced pressure, the residue triturated with hexane, the residue dissolved in water, the water solution repeatedly extracted with ethyl acetate and the dried (MgSO$_4$) ethyl acetate solution evaporated; yield 44%, m.p. 181°–182° C. EtOAc $^1$H NMR (DMSO-d$_6$): δ2.75–3.6 (CH$_2$,m), 5.4 (CH), 8.7 (H-4, H-6).

EXAMPLE 31

2-[3-(1-Perhydroazocinyl)propyl]thio-5-chloropyrimidine

5-Chloropyrimidine-2-thione (2 mmol) and potassium tert-butoxide (2 mmol) was stirred together in DMF (20 ml) for 5 min at room temperature before 1-(3-chloropropyl)perhydroazocine (2 mmol) was added. The mixture was stirred for 2 days at room temperature and for 2 hours at 80° C. The solution was evaporated, the residue triturated with water, extracted with chloroform and the dried (MgSO$_4$) chloroform solution evaporated. The oily product which remained (0.47 g) was the title compound; yield 45% $^1$H NMR (CDCl$_3$): 1.3–2.8 (9×CH$_2$), 3.20 (SCH$_2$), 8.40 (H-4, H-6). The compound was further characterized as a solid by conversion into its HCl salt using HCl in ethanol; m.p. 154° C. (acetone).

EXAMPLE 32

2-[N-(4-phenylazetidin-2-one)methyl]thio-6-chloropyrimidine

Potassium tert-butoxide (2 mmol) was added to a solution of 4-phenylazetidin-2-one (2 mmol) in DMF (25 ml) and the mixture stirred for 5 min before 2-(iodomethyl)thio-5-chloropyrimidine (2.0 mmol) in DMF solution (10 ml) was added. The mixture was stirred at room temperature overnight, the solvent distilled off at reduced pressure, the residue triturated with water, the insoluble material dissolved in chloroform, the dried (MgSO$_4$) chloroform solution evaporated and the residue chromatographed on a silica gel column using chloroform; yield 33%. m.p. 52° C. $^1$H NMR (CDCl$_3$): δ2.8–3.5 (CH$_2$CO,m), 4.5–4.7 (CH), 4.6 and 5.2 (CH$_2$, J 14 Hz). 7.3 (Ph), 8.2 (H-4, H-6). IR (CHCl$_3$): 1760 cm$^{-1}$ (CO).

EXAMPLE 33

2-(2,4-dihydro-5(7)-methyl-7(5)-phenyl-1H-1,4-diazepin-6-yl)thio-5-chloropyrimidine HClO$_4$ A solution of 2,4-dihydro-6-chloro-5(7)-methyl-7(5)-phenyl-1H-1,4-diazepine HClO$_4$ (1,4 mmol) in acetonitrile (5 ml) was added to a mixture of the potassium salt of 5-chloropyrimidine-2-thione (1.4 mmol) in acetonitrile (20 ml) and the resultant mixture heated under reflux for 3 hours. The solid was then removed by filtration with water, the water as well as the solid residue extracted with ethyl acetate, the dried (MgSO$_4$) ethyl acetate solution evaporated and the residue recrystallized from dilute MeOH; yield 66%, m.p. 222° C. $^1$H NMR (acetone -d$_6$) δ2.6 (Me), 4.1 (CH$_2$CH$_2$), 7.3 (Ph), 8.60 (H-4, H-6).

EXAMPLE 34

2-(2,4-dihydro-5(7)-methyl-7(5)-phenyl-1,4-diazepine-6-methyl)thio-5-chloropyrimidine. HCl (a)

2,4-dihydro-6-chloromethyl-5(7)-methyl-7(5)-phenyl-1H-1,4-diazepine. HClO$_4$

Paraformaldehyde (7 mmol) was added to a solution of 1H-2,4-dihydro-5(7)-methyl-7(5)-phenyl-1,4-diazepine. HClO$_4$ (5.2 mmol) in conc. HCl (10 ml). The mixture was stirred at room temperature for 15 min before the product was filtered off; yield 1.30 g. $^1$H NMR (acetone-d$_6$): δ2.7 (Me), 3.9 (CH$_2$CH$_2$), 4.4 (CH$_2$Cl), 7.5 (Ph).

(b)

2-(2,4-dihydro-5(7)-methyl-7(5)-phenyl-1H-1,4-diazepine-6-methyl)thio-5-chloropyrimidine. HCl 5-chloropyrimidine-2-thione (2 mmol) and triethylamine (0.28 ml, 2 mmol) were stirred together in dichloromethane (20 ml) until all the material had dissolved. N-(1H-2,4-dihydro-6-chloromethyl-5(7)-methyl-7(5)-phenyl-1H-1,4-diazepine HClO$_4$ (0.68 g, 2 mmol) was then added, the mixture was heated under reflux for 1 h, the solvent distilled off, the residue triturated with water, the insoluble material extracted with CHCl$_3$ EtOAc, the dried (MgSO$_4$) organic solution evaporated and the residue recrystallized from EtOAc: acetone: pet. ether: yield 69%, m.p. 225° C. $^1$H NMR (acetone-d$_6$): δ2.6 (Me), 3.9 (CH$_2$CH$_2$) 4.0 (CH$_2$S), 7.5 (Ph), 8.50 (H-4, H-6).

EXAMPLE 35

2-(Pyrimidin-2-yl)thio-5-bromopyrimidine

2-Chloro-5-bromopyrimidine (10 mmol) was added to a solution of pyrimidine-2-thione (10 mmol) in ethanolic 0.24 M NaOEt (45 ml), the mixture heated under reflux for 2 hours, the solvent distilled off, the residue extracted with chloroform (70 ml), the chloroform solution shaken with 2 M NaOH and with water, the dried (MgSO$_4$) solution evaporated and the residue repeatedly extracted with pet. ether leaving the title compound. Yield 35%, m.p. 178°–180° C. (iPrOH). $^1$H NMR (CDCl$_3$): δ7.13 (H-5'), 8.60 (H-4', H-6'), 8.66 (H-4, H-6).

EXAMPLE 36

2-(2-Thienylmethoxycarbonylmethyl)thio-4,6-dimethyl-5-bromopyrimidine (a) 2-Thienylmethyl bromoacetate:

A solution of bromoacetyl chloride (60 mmol) and 2-hydroxymethylthiophene (60 mmol) in benzene (100 ml) was heated under reflux for 90 min, the cold solution shaken with saturated NaHCO$_3$ aq., the dried (MgSO$_4$) solution evaporated and the residue fractionally distilled; yield 48%, b.p. 96° C./0.05 mmHg. $^1$H NMR (CDCl$_3$) δ3.80 (CH$_2$), 5.30 (OCH$_2$), 7.00 and 7.26 (thiophene).

(b)
2-(2-Thienylmethoxycarbonylmethyl)thio-4,6-dimethyl-5-bromopyrimidine

The above ester (6.6 mmol) was added to a mixture of 4,6-dimethyl-5-bromopyrimidine-2-thione. HCl (6 mmol) and triethylamine (15 mmol) in dichloromethane (50 ml), the mixture stirred at room temperature for 1 day, more dichloromethane (50 ml) added, the mixture shaken with 1 M NaOH and water (10 ml), the dried (MgSO$_4$) solution evaporated and the residue chromatographed on silica gel 60 (Merck, 25 g) using ether; yield 80% of a pale yellow oil. $^1$H NMR (CDCl$_3$) δ2.46 (Ml), 3.86 (SCH$_2$), 5.26 (OCH$_2$), 6.96 and 7.23 (thiophene).

EXAMPLE 37

2-(N-Methylcarbamoyl)thio-5-chloropyrimidine

A mixture of 5-chloropyrimidine-2-thione (3 mmol) and methylisocyanate (4 mmol) in dichloromethane (15 ml) was stirred at room temperature for 2 h, the solvent was then distilled off and the residue was crystallised from CHCl$_3$: Pet. ether; yield 85%, m.p. 115° C. $^1$H NMR (CDCl$_3$) δ3.03 (Me), 8.62 (H-4, H-6).

EXAMPLE 38

2-(2,3,5-Tri-O-benzoyl-β-D-ribofuranosyl)thio-5-chloropyrimidine

A mixture of 5-chloropyrimidine-2-thione (4.3 mmol), 2,3,5-tri-O-benzoyl-β-D-ribofuranosyl chloride (4.3 mmol) and triethylamine (4.3 mmol) in dichloromethane (25 ml) was stirred together at room temperature for 4 h, the mixture evaporated and the residue triturated with water; the residue was the title compound; yield 28% $^1$H NMR (CDCl$_3$): δ4.75 (CH$_2$), 6.0–6.5 (4 H), 7.2–8.2 (3 Ph), 8.50 (H-4, H-6).

EXAMPLE 39

2-Methylsulfinyl-5-chloropyrimidine

A solution of 2-methylthio-5-chloropyrimidine (13 mmol) in chloroform (85 ml) was cooled to −20° C. and m-chloroperbenzoic acid (17 mmol) added with stirring. The mixture was stirred for 40 min at −20° C. and for 4 h at 0° C. and left at this temperature overnight. The chloroform solution was then washed with 1 M potassium carbonate (3×10 ml) and the dried (MgSO$_4$) solution evaporated. The residual oily material crystalized on standing; yield 80% m.p. 48° C. (n-heptane). $^1$H NMR (CDCl$_3$): δ2.93 (Me), 8.83 (2H-4,6).

EXAMPLE 40

2-(2-Thienylmethyl)sulfinyl-5-bromopyrimidine

85% m-Chloroperbenzoic acid (1.5 mmol) was added to a solution of 2-(2-thienylmethylthio)-5-bromopyrimidine (1.5 mmol) in dichloromethane (25 ml) at −10° C. and the solution left at 0° C. for 18 h. The dichloromethane solution was then washed with saturated aqueous solutions of Na$_2$SO and NaHCO$_3$, and the dried (MgSO$_4$) solution evaporated to leave the title compound; yield 53%, m.p. 108°–109° C. (iPrOH). $^1$H NMR (CDCl$_3$) δ4.53 (CH$_2$, 6.9 (H-3', H-4'), 7.16 (H-5'), 8.83 (H-4, H-6).

EXAMPLE 41

2-Benzylsulfinyl-5-chloropyrimidine

The oxidation of 2-benzylthio-5-chloropyrimidine was carried out using one molar equivalent of 85% m-chloroperbenzoic acid in dichloromethane, initially at −10° C. and then at 0° C., as described in Example 40 above; yield 88%, m.p. 92° C. (iPrOH). $^1$H NMR (CDCl$_3$) δ4.30 and 4.33 (CH$_2$), 7.23 (Ph), 8.73 (H-4, H-6).

EXAMPLE 42

2-(Iodomethyl)sulfinyl-5-chloropyrimidine

90% m-chloroperbenzoic acid 8.4 mmol) in chloroform (8 ml) was added dropwise for 10 min with stirring to a solution of 2-(iodomethyl)thio-5-chloropyrimidine in chloroform (7 ml) at −5° C. The reaction mixture was coloured violet during the addition. The mixture was left at room temperature overnight. The chloroform solution was then extracted with 1 M K$_2$CO$_3$, washed with a little water, then dried (MgSO$_4$) solution evaporated and the product subjected to thick-layer chromatography. 2-(Iodomethyl)sulfinyl-5-chloropyrimidine: yield 24%, m.p. 158° C., IR (KBr): 1050 and 1090 cm$^{-1}$ (SO).

2-Iodomethyl)sulfonyl-5-chloropyrimidine was formed as a by product in a yield of 17% m.p. 152° C.

EXAMPLE 43

2-(Chloromethyl)sulfinyl-5-chloropyrimidine

90% m-chloroperbenzoic acid (4.2 mmol) in chloroform (7 ml) was added dropwise over 40 min to a solution of 2-(chloromethyl)thio-5-chloropyrimidine (3.9 mmol) in chloroform (6 ml) with stirring at −5° C. The mixture was allowed to reach room temperature and stirred overnight, washed with 1 M K$_2$CO$_3$, the dried (MgSO$_4$) chloroform solution evaporated and the residue recrystallized from benzene/petroleum ether (60°–80° C.); yield 73%, m.p. 90° C. $^1$H NMR (CDCl$_3$): δ4.70 and 5.00 (2H-CO$_2$SO, J$_{gem}$ 10 Hz), 8.84 (H-4, H-6).

EXAMPLE 44

2-(4-Chlorophenoxymethyl)sulfinyl-5-chloropyrimidine

Method A: 85% m-chloroperbenzoic acid (1.76 mmol) was added to a solution of 2-(4-chlorophenoxymethyl)thio-5-chloropyrimidine (1.5 mmol) in dichloromethane 70 ml) at −10° C. The solution was left at 0°–5° C. for 18 h, concentrated and applied on a column of Silica gel 60 (Merck; 25 g). Unreacted sulfide was eluted with diethyl ether and the sulfoxide with ethyl acetate; yield 51%, m.p. 88°–90° C. $^1$H NMR (CDCl$_3$) δ5.28 and 5.33 (CH$_2$) 6.95 and 7.28 (PhH), 8.85 (H-4, H-6).

EXAMPLE 45

2-Methylsulfinyl-5-bromopyrimidine

The title compound was prepared by oxidation of 2-methylthio-5-bromopyrimidine by m-chloroperbenzoic acid in chloroform as described in Example 39; yield 90%, m.p. 90° C. (n-heptane). $^1$H NMR (CDCl$_3$): δ2.91 (Me),. 8.90 (H-4, H-6).

EXAMPLE 46

2-Benzylsulfinyl-5-bromopyrimidine

The oxidation of 2-benzylthio-5-bromopyrimidine was carried out using one molar equivalent of 85% m-chloroperbenzoic acid in dichloromethane, initially at −10° C. and then at 0° C., as described in Example 40 above; yield 91%, m.p. 101° C. (iPrOH). $^1$H NMR (CDCl$_3$); δ4.26 and 4.31 (CH$_2$), 7.16 (Ph), 8.80 (H-4, H-6).

EXAMPLE 47

2-Phenylsulfinyl-5-chloropyrimidine

30% hydrogen peroxide solution (0.8 g) was added to a solution of 2-phenylthio-5-chloropyrimidine (5 mmol) in acetic acid (4 ml) and left at room temperature for 60 h). The solution was then diluted (25 ml) and the precipitate purified by thick-layer (2 mm) chromatography on silica gel 60F (Merck). The plates were developed with EtOAc; yield 50% m.p. 115° C. (ligroin). $^1$H NMR (CDCl$_3$): δ7.4 and 7.8 (Ph), 8.71 (H-4, H-6).

EXAMPLE 48

2-Allylsulfinyl-5-chloropyrimidine

30% Hydrogen peroxide (50 mmol) was added to a solution of 2-allylthio-5-chloropyrimidine (10 mmol) in acetic acid (15 ml) and the mixture stirred at room temperature for 24 h. The resultant solution was concentrated at reduced pressure to a small volume, water (20 ml) added and the mixture extracted with chloroform, the chloroform solution washed with potassium carbonate solution, the dried (MgSO$_4$) solution evaporated and the residue crystallized from chloroform: pet. ether; yield 78%, m.p. 82° C. $^1$H NMR (CDCl$_3$): δ3.7–4.0 (CH$_2$, 5.0–6.2 (3H, CH$_2$=CH), 8.86 (H-4, H-6).

EXAMPLE 49

2-(5-Chloropyrimidine-2-thiomethyl)sulfinyl-5-chloropyrimidine and 2-(5-chloropyrimidine-2-sulfinylmethyl)sulfonyl-5-chloropyrimidine 30% Hydrogen peroxide (2 ml) was added to a solution of bis(5-chloropyrimidine-2-thio)methane (1.3 mmol) in acetic acid (10 ml) and the mixture stirred at room temperature for 6 h. The mixture was then concentrated to a small volume at reduced pressure, water (20 ml) added, the mixture extracted the chloroform (3×20 ml), the dried (MgSO$_4$) chloroform solution evaporated, the residue extracted with acetone, the insoluble material filtered off and recrystallized from DMSO; yield 22%, m.p. 250° C. The product is the 2-(5-chloropyrimidine-2-sulfinylmethyl)sulfonyl-5-chloropyrimidine. $^1$H NMR (DMSO-d$_6$/CDCl$_3$): δ5.31 and 5.63 (CH$_2$, d, J 14 Hz), 906 (H'-4, H'-6), 9.14 (H-4, H-6). IR (KBr): 1340, 1140 and 1130 (SO$_2$), 1080 (SO)). The acetone solution from the extraction was evaporated and the residual 2-(5-chloropyrimidine-2-thiomethyl)sulfinyl-5-chloropyrimidine crystallized from ethanol; yield 48%; m.p. 140° C. $^1$H NMR (CDCl$_3$): δ4.73 and 4.93 (CH$_2$, d, J 13 Hz), 8.56 (H'-4, H'-6), 8.81 (H-4, H-6). IR(KBr): 1080 cm$^{-1}$ (SO).

EXAMPLE 50

2-Propargylsulfinyl-5-chloropyrimidine

A mixture of selenium dioxide (4 mmol) and 35% H$_2$O$_2$ (4 mmol) in water (2.5 ml) was added to a solution of 2-propargylthio-5-chloropyrimidine in methanol (10 ml). The mixture was stirred at room temperature for 18 h before water (50 ml), saturated with NaCl, was added and the mixture extracted with chloroform (3×20 ml). The dried (MgSO$_4$) chloroform solution was evaporated and the residue recrystallized from chloroform: pet. ether; yield 63%, m.p. 92° C. $^1$H NMR (CDCl$_3$): δ2.28 (HC≡t, J 2 Hz), 3.87 and 4.09 (CH$_2$ J 15 Hz), 8.85 (H-4, H-6), IR (KBr): 3235 (CH≡), 2110 and 2100 (—C≡C—). MS [70 eV; m/e (% rel. int)]: 200 (13, M) 199 (19), 173 (33), 171 (100), 146 (25), 114 (30), 113 (31), 111 (47).

EXAMPLE 51

2-(2,3-Epoxypropyl)sulfinyl-5-chloropyrimidine

A mixture of 35% H$_2$O$_2$ (1.9 mmol) and SeO$_2$ (1.9 mmol) in water (1.5 ml H$_2$O) was added to a solution of 2-(2,3-epoxypropyl)thio-5-chloropyrimidine (1.9 mmol) in methanol (7 ml). The mixture was stirred at room temperature for 4 h before saturated NaCl aq. (30 ml) was added and the mixture extracted with chloroform (3×15 ml). The dried (MgSO$_4$) chloroform solution was evaporated and the residue purified by preparative TLC on silica gel using CHCl$_3$: EtOH (95:5); yield 24%, m.p. 92° C. $^1$H NMR (CDCl$_3$): δ2.4–3.6 (5H, m), 8.84 (H-4, H-6). IR (KBr): 1050 cm$^{-1}$ (SO).

EXAMPLE 52

2-(2-Hydroxy-3-chloropropyl)sulfinyl-5-chloropyrimidine

A solution of 35% H$_2$O$_2$ (1.7 mmol) and SeO$_2$ (1.7 mmol) in water (2.5 ml) was added to a solution of 2-(2-hydroxy-3-chloropropyl)thio-5-chloropyrimidine (1.7 mmol) in methanol (10 ml). The mixture was stirred at room temperature for 18 h before saturated NaCl aq. (40 ml) was added and the mixture extracted with chloroform (3×20 ml). The dried (MgSO$_4$) chloroform solution was evaporated and the residue crystallized from ethyl acetate; yield 59%; m.p. 170° C. $^1$H NMR (DMSO-d$_6$): δ3.0–4.4 (6H, m), 9.10 (H-4, H-6). IR (KBr): 3400 (OH), 1060–1070 cm$^{-1}$ (SO).

EXAMPLE 53

2-[3-(1-Perhydroazocinyl)propyl]sulfinyl-5-chloropyridimide

A solution from (SeO$_2$ 1.3 mmol) and 35% H$_2$O$_2$ (1.3 mmol) in water (2 ml) was added to a solution of 2-[3-(perhydroazocinyl)propyl]thio-5-chloropyrimidine (1.3 mmol) in methanol (10 ml), the resultant solution stirred at room temperature overnight, saturated NaCl aq. solution added, the mixture extracted with chloroform (10×15 ml), the dried (MgSO$_4$) chloroform solution evaporated and the residue well washed with acetone; yield 44%, m.p. 160° C. $^1$H NMR (DMSO-d$_6$/CDCl$_3$): δ1.4–1.6 and 2.9–3.5 (10×CH$_2$), 9.0 (H-4, H-6). IR (KBr): 1080 cm$^{-1}$ (SO).

EXAMPLE 54

2-Iodomethylsulfonyl-5-chloropyrimidine

90% m-chloroperbenzoic acid (8.4 mmol) in chloroform (8 ml) was added dropwise for 10 min with stirring to a solution of 2-iodomethylthio-5-chloropyrimidine in chloroform (7 ml) at −5° C. The reaction mixture was coloured violet during the addition. The mixture was left at room temperature overnight. The chloroform solution was then extracted with 1 M K$_2$CO$_3$, washed with a little water, the dried (MgSO$_4$) solution evaporated and the product subjected to thick layer chromatography. 2-(Iodomethyl)sulfonyl-5-chloropyrimidine was obtained in a yield of 17% (together with 2-(iodomethyl) sulfinyl-5-chloropyrimidine).

EXAMPLE 55

2-(Chloromethyl)sulfonyl-5-chloropyrimidine

90% m-chloroperbenzoic acid (9.4 mmol) in chloroform (9 ml) was added dropwise over 30 min to a solution of 2-(chloromethyl)thio-5-chloropyrimidine (4.2 mmol) in chloroform (6 ml) with stirring at −5° C. The mixture was allowed to reach room temperature, and stirred overnight. The mixture was then washed with 1 M K$_2$CO$_3$, the dried (MgSO$_4$) chloroform solution evaporated and the residue recrystallized from ethanol; yield 63%, m.p. 100° C. $^1$H NMR (CDCl$_3$): δ5.02 (2H—CH$_2$), 8.88 (H-4, H-6).

EXAMPLE 56

Diethyl(5-chloropyrimidine-2-sulfonyl)methanephosphonate

90% m-chloroperbenzoic acid (8 mmol) was added dropwise with stirring over 5 min to a solution of diethyl (5-chloropyrimidine-2-thio)methanephosphonate (2.7 mmol) in chloroform (15 ml) at −5° C. The reaction mixture was allowed to reach room temperature and stirred overnight. The mixture was then extracted with 1 M K$_2$CO$_3$, the chloroform solution dried (MgSO$_4$), the solvent evaporated and the residue recrystallized from benzene:petroleum ether (60°–80° C.); yield 90%, m.p. 119° C. $^1$H NMR (CDCl$_3$): δ1.38 (6H, 2Me), 3.9–4.5 (6H, 2 OCH$_2$ and CH$_2$P), 8.92 (H-4, H-6).

EXAMPLE 57

2-Allylsulfonyl-5-chloropyrimidine m-chloroperbenzoic acid (90%; 6 mmol) was added to a solution of 2-allylthio-5-chloropyrimidine (2.3 mmol) in chloroform (10 ml) and the mixture stirred at 40° C. for 90 min. The cold reaction mixture was extracted with aqueous potassium carbonate, the chloroform solution dried (MgSO$_4$), the solution evaporated and the residue crystallized from methanol; yield 70%, m.p. 84° C. $^1$H NMR (CDCl$_3$): δ4.24 (CH$_2$, J 7 Hz), 5.1–6.2 (CH=CH$_2$), 8.90 (H-4, H-6).

EXAMPLE 58

1-(3-Oxobuten-1-yl)sulfonyl-5-chloropyrimidine

90% m-chloroperbenzoic acid (11.5 mmol) chloroform (10 ml) was added to a solution of 2-(3-oxobuten-1-yl)thio-5-chloropyrimidine in chloroform (10 ml) and the mixture stirred at 40° C. for 2 h. The cold reaction mixture was extracted with aqueous KHCO$_3$, and the dried (MgSO$_4$) chloroform solution evaporated; yield 92%. The cis/trans isomers could be separated by thick layer chromatography (silica gel; CHCl$_3$: EtOAc (1:1)).

(E): m.p. 117° C. (MeOH). $^1$H NMR (acetone-d$_6$): δ2.43 (Me), 7.12 and 7.68 (Hα, Hβ, d, J 16 Hz), 9.10 (H-4, H-6) (Z): m.p. 95° C. (MeOH). $^1$H NMR (acetone-d$_6$): δ2.32 (Me), 6.97 and 7.13 (Hα, Hβ, d,J 12 Hz), 9.10 (H-4, H-6).

EXAMPLE 59

2-(1,2-Propadienyl)sulfonyl-5-chloropyrimidine

90% m-chloroperbenzoic acid (13 mmol) in chloroform (20 ml) was added dropwise over 30 min to a solution of the isomeric 2-propargylthio-5-chloropyrimidine and 2-(1,2-propadienyl)thio-5-chloropyrimidine (3.5 g; ratio 3:2) in chloroform (30 ml) with stirring at −5° C. The mixture was allowed to reach room temperature and stirred overnight. The mixture was then washed with 2 M $K_2CO_3$, the dried ($MgSO_4$) chloroform solution evaporated and the residue crystallized from methanol. The yield of 2-(1,2-propadienyl)sulfonyl-5-chloropyrimidine was 74%, m.p. 130° C. During the conditions of the oxidation with m-chloroperbenzoic acid the propargyl isomer was completely isomerized to the allene isomer. $^1$H NMR (acetone-$d_6$): δ5.65 (CH, t, J 6 Hz), 6.73 (CH, t, J 6 Hz), 9.04 (H-4, H-6, s). IR (KBr); 1960 and 1920 (allene), 1330 and 1140 ($SO_2$).

EXAMPLE 60

2-(2-Thienylmethylsulfonyl)-5-bromopyrimidine

A solution of 2-(2-thienylmethylthio)-5-bromopyrimidine (3 mmol) and 85% m-chloroperbenzoic acid (9 mmol) in dichloromethane (80 ml) was left at room temperature for 1 day. The solution was then washed with saturated $Na_2SO_3$ (3×15 ml), washed with saturated $NaHCO_3$ (3×10 ml) and the dried ($MgSO_4$) dichloromethane solution evaporated to yield the title compound; yield 70%, m.p. 124°–126° C. (iPrOH). $^1$H NMR ($CDCl_3$): δ4.93 ($CH_2$, 6.9, (H-3', H-4') 7.20 (H-5'), 8.93 (H-4, H-6).

EXAMPLE 61

2-Phenacylsulfonyl-5-bromopyrimidine

2-Phenacylthio-5-bromopyrimidine was oxidised to the sulfone by means of m-chloroperbenzoic acid as described in Example 61 yield 91%; m.p. 95° C. (iPrOH). $^1$H NMR ($CDCl_3$): δ5.16 ($CH_2$), 7.5–7.8 (Ph), 8.92 (H-4, H-6).

EXAMPLE 62

2-Benzylsulfonyl-5-bromopyrimidine

A solution of 2-benzylthio-5-bromopyrimidine (10.6 mmol) and 85% m-chloroperbenzoic acid (31.8 mmol) in dichloromethane (200 ml) ws left at room temperature for 3 days before the reaction mixture was worked up as in Example 61 above; yield 93%, m.p. 142°–143° C. (iPrOH). $^1$H NMR ($CDCl_3$): δ4.73 ($CH_2$), 7.26 (Ph), 8.90 (H-4, H-6).

EXAMPLE 63

2-(2-Thienyl)sulfonyl-5-chloropyrimidine

A solution of 2-(2-thienyl)thio-5-chloropyrimidine (6 mmol) and 85% m-chloroperbenzoic acid (15.3 mmol) in dichloromethane (150 ml) was left at room temperature for 2 days. Additional dichloromethane (100 ml) was then added, the solution shaken with saturated $Na_2SO_3$ aq. (3×20 ml), with saturated $NaHCO_3$ aq. (2×20 ml), the dried ($MgSO_4$) solution evaporated and the residue crystallized from ethanol; yield 90%, m.p. 116°–117° C. $^1$H NMR ($CDCl_3$): δ7.1–7.8 (thiophene), 8.80 (H-4, H-6).

EXAMPLE 64

2-Benzylsulfonyl-4,6-dimethyl-5-bromopyrimidine

A solution of 2-benzylthio-4,6-dimethyl-5-bromopyrimidine (5 mmol) and 85% m-chloroperbenzoic acid (15.9 mmol) in dichloromethane (100 ml) was left at room temperature for 3 days. The solution was then shaken with saturated $Na_2SO_3$ aq. (3×15 ml), saturated $NaCHO_3$ aq. (3×10 ml) and the dried $MgSO_4$ solution evaporated to leave the sulfone; yield 94%, m.p. 138°–139° C. (iPrOH). $^1$H NMR (TFA): δ2.83 (Me), 4.93 ($CH_2$), 7.33 (Ph).

EXAMPLE 65

2-(Carbamoylmethyl)sulfonyl-4,6-dimethyl-5-bromopyrimidine

A solution of 2-(carbamoylmethyl)thio-4,6-dimethyl-5-bromopyrimidine (2.16 mmol) and 85% m-chloroperbenzoic acid (6.48 mmol) in dichloromethane (75 ml) was left at room temperature for 3 days. The solution was then shaken with saturated $Na_2SO_3$ aq., saturated $NaHCO_3$ aq. and the dried ($MgSO_4$) solution evaporated to leave the sulfone; yield 72%, m.p. 175°–177° C. (iPrOH). $^1$H NMR (DMSO-$d_6$): δ2.50 (Me), 3.80 ($CH_2$).

EXAMPLE 66

2-Phenylsulfonyl-5-chloropyrimidine

30% hydrogen peroxide solution (2 g) was added to a solution of 2-phenylthio-5-chloropyrimidine (18 mmol) in acetic acid (14 ml). After 2 days at room temperature another 2 g of 30% hydrogen peroxide solution was added and the resultant solution heated at 50° C. for 4 h. The sulfone was precipitated on dilution of the cold solution (100 ml); yield 80%, m.p. 103° C. (ETOH). $^1$H NMR ($CDCl_3$): δ7.6 and 8.1 (Ph, m) 8.83 (H-4, H-6).

EXAMPLE 67

Phenylsulfonyl-5-bromopyrimidine

2-Phenylthio-5-bromopyrimidine (prepared as was oxidised by hydrogen peroxide as described for the chloro analogue in Example 43; yield 75%, m.p. 103° C. (iPrOH). $^1$H NMR ($CDCl_3$): δ7.6 and 8.1 (Ph, m) 8.90 (H-4, H-6).

EXAMPLE 68

2-Methylsulfonyl-4-methoxycarbonyl-5-chloropyrimidine

A solution of 2-methylthio-4-methoxycarbonyl-5-chloro-pyrimidine (10 mmol) and 30% hydrogen peroxide (2.5 g) in acetic acid (8 ml) was left at room temperature for 3 d. The mixture was then poured onto ice, the mixture neutralised with sodium bicarbonate and extracted with chloroform, and the chloroform solution evaporated. The oily residue slowly crystallised on standing; yield 74%, m.p. 96° C. (EtOH). $^1$H NMR ($CDCl_3$): δ3.38 $SO_2$Me), 4.06 (OMe), 7.91 (H-6).

EXAMPLE 69

2-Methylsulfonyl-4-N,N-diethylaminocarbonoyl-5-bromopyrimidine

Chlorine was passed for ca. 6 min into an ice-cold suspension of 2-methylthio-4-N,N-diethylaminocarbonylpyrimidine (15 mmol) in water (70 ml) with vigorous stirring. After stirring for 30 min in the ice-bath chlorine was again passed into the mixture for ca. 6 min. After stirring for an addition 20 min the mixture was neutralised with sodium bicarbonate, extracted with chloroform, the chloroform solution washed and dried ($MgSO_4$) and the solvent distilled off; yield 86%, m.p. 141° C. (iPrOH). $^1$H NMR ($CDCl_3$): δ1.23 and 3.13/3.61 ($NEt_2$), 3.33 ($SO_2$Me), 9.08 (H-6).

EXAMPLE 70

2-Benzylsulfonyl-5-chloropyrimidine

A solution of 2-benzylthio-5-chloropyrimidine (3.7 mmol) and potassium permanganate (5.2 mmol) in 1 N acetic acid (12 ml) was kept at room temperature until TLC (silica gel with EtOAc) showed the oxidation to be complete (ca. 30 min). The mixture was then diluted and neutralized with sodium bicarbonate. The precipitate was collected by filtration, sucked dry and washed with chloroform. The chloroform washing was used to extract the aqueous filtrate, the chloroform solution washed with a little water, dried (MgSO$_4$) and evaporated. Yield 30%, m.p. 122°–124° C. (iPrOH). $^1$H NMR (CDCl$_3$): δ4.75 (CH$_2$), 7.28 (Ph), 8.83 (2H-4.6).

EXAMPLE 71

2-(2,3,4,6-Tetraacetylglucopyranosyl)sulfonyl-5-chloropyrimidine 2-(2,3,4,6-Tetraacetylglucopyranosyl)thio-5-chloropyrimidine (1.0 mmol) was dissolved in acetic acid (10 ml) and a solution of KMnO$_4$ (1.5 mmol) in water (5 ml) was added. The mixture was stirred at 40° C. and additional amounts of KMnO$_4$ (3×0.15 g, 0.9 mmol) were added at intervals of 2.5 h, 1 d, 2 d and 1 d and after 1 additional day the reaction was stopped. An aqueous solution of NaHSO$_3$ was then added until all the MnO$_2$ has dissolved and the product, precipitated by addition of water and crystallized from EtOH; yield 30%, m.p. 180° C. $^1$H NMR (CDCl$_3$): δ1.8–2.0 (Ac), 3.5–6.0 (glucose), 8.90 (H-4, H-6).

EXAMPLE 72

2-(5-Chloropyrimidin-2-oxymethyl)sulfonyl-5-chloropyrimidine

The molybdenum complex MoO$_5$.HMPA.H$_2$O (1.9 mmol) was added to a solution of 2-(5-chloropyrimidin-2-oxymethyl)thio-5-chloropyrimidine (0.76 mmol) in dichloromethane (10 ml) and the mixture stirred at room temperature for 18 h. The reaction mixture was then washed with water (30 ml), the washings extracted with chloroform, the combined chloroform solutions extracted with 1 M K$_2$CO$_3$, the dried (MgSO$_4$) chloroform solution evaporated and the residue crystallized from chloroform:pet. ether; yield 48%, m.p. 135° C. $^1$H NMR (CDCl$_3$): δ6.03 (CH$_2$) 8.41 (H'-4, H'-6), 8.86 (H-4, H-6).

EXAMPLE 73

2-(Iodomethyl)sulfonyl-5-chloropyrimidine

MoO$_5$ HMPA H$_2$O (5 mmol) in dichloromethane (15 ml) was added to a solution of 2-(iodomethyl)thio-5-chloropyrimidine (2 mmol) in dichloromethane (5 ml). The mixture was stirred at room temperature for 2 days before washing with water. The washings were extracted with dichloromethane (3×15 ml), and the combined dichloromethane solution washed with 1 M K$_2$CO$_3$, the dried dichloromethane (MgSO$_4$) was evaporated and the residue crystallized from ethanol: yield 52%, m.p. 152° C. $^1$H NMR (CDCl$_3$): δ4.89 (CH$_2$), 8.90 (H-4, H-6).

EXAMPLE 74

2-(4-Tolysulfonyl)-5-bromopyrimidine

A mixture of 2-chloro-5-bromopyrimidine (3.6 mmol), p-toluenesulfinic acid Na-salt (6 mmol), TEBA (6 mmol) and LiBr (1.0 g) in EtOH (30 ml) was heated under reflux for 20 h when TLC monitoring (silica gel/benzene) showed the reaction to be complet. The solvent was removed as reduced pressure, water (25 ml) added to the residue, the aqueous solution left at 0° C. and the precipitate collected and extracted with chloroform. Evaporation of the chloroform solution left the title compound; yield 22%, m.p. 142°–144° C. (iPrOH). $^1$H NMR (CDCl$_3$): δ2.43 (Me), 7.30 and 7.96 (Ph), 8.90 (H-4, H-6).

EXAMPLE 75

2-(4-Tolyl)sulfonyl-5-iodopyrimidine

A mixture of 2-chloro-5-iodopyrimidine [(7.5 mmol), p-toluenesulfinic acid Na-salt (12.1 mmol) and catalytic amounts of iodine and Cu-powder in ethanol (90 ml) was heated under reflux for 3 days. The solvent was then distilled off, the residue extracted with chloroform, the chloroform solution washed with aq. saturated NaHCO$_3$ and the dried (MgSO$_4$) solution evaporated to leave the sulfone; yield 10%, m.p. 138°–139° C. (iPrOH). $^1$H NMR (CDCl$_3$): δ2.43 (Me), 7.30 and 7.93 (Ph), 9.02 (H-4, H-6).

EXAMPLE 76

2-(4-Tolyl)sulfonyl-4,6-dimethyl-5-bromopyrimidine

A mixture of 2-chloro-4,6-dimethyl-5-bromopyrimidine (5 mmol) p-toluenesulfinic acid Na-salt (8.3 mmol) and catalytic amounts of iodine and Cu-powder in ethanol (60 ml) was heated under reflux for 3 days. The solvent was then distilled off, the residue extracted with chloroform (100 ml), the chloroform solution washed with aq. saturated NaHCO$_3$ and the dried (MgSO$_4$) solution evaporated to leave the sulfone; yield 23%, m.p. 157°–158° C. (iPrOH). $^1$H NMR (DMSO-d$_6$): δ2.43 (Me-Ph), 2.63 (4-Me, 6-Me), 7.43 and 7.86 (Ph).

EXAMPLE 77

2-(trans-Styryl)sulfonyl-5-chloropyrimidine

Sodium hydride dispersion (55–60%, 2 mmol) was further dispersed in benzene (4 ml) and added gradually to a solution of diethyl (5-chloropyrimidin-2-sulfonyl)-methanephosphonate (0.66 g, 2 mmol) in benzene (4 ml). The mixture was stirred for 10 min before a solution of benzaldehyde (0.21 g, 2 mmol) in benzene (2 ml) was added. The resultant mixture was stirred at room temperature overnight before extraction with water. Evaporation of the dried (MgSO$_4$) benzene solution left the product which was recrystallised from ethanol; yield 0.20 g 35%, m.p. 150° C. $^1$H NMR (CDCl$_3$): δ7.24 and 7.90 (2H-vinyl, J$_{vic}$ 16 Hz), 7.60 (Ph, m.), 8.90 (2H-4,6).

EXAMPLE 78

2-(2-2'-Furylvinyl)sulfonyl-5-chloropyrimidine

Sodium hydride dispersion (55–60%, 0.084 g, 2 mmol) was added to ethylene glycol dimethyl ether (4 ml) and the mixture gradually added to a solution of diethyl (5-chloropyrimidin-2-sulfonyl)-methanephosphonate (0.66 g, 2 mmol). The mixture was stirred for 10 min before a solution of furfural (0.19 g, 2 mmol) in ethylene glycol dimethyl ether (2 ml) was added. The resultant mixture was stirred at room temperature overnight. The insoluble material was then removed by filtration, the filtrate evaporated to dryness and the residue crystallised from ethanol; yield 0.14 g 26%, m.p.

140° C. ¹H NMR (CDCl₃): δ6.4–7.8 (2H vinyl, 3H-furyl, m) 8.90 (2H-4.6).

EXAMPLE 79

2-(5-Nitro-2-thienyl)sulfonyl-5-chloropyrimidine

A solution from 2-(5-nitro-2-thienyl)thio-5-chloropyrimidine (1.2 mmol) and 85% m-chloroperbenzoic acid (3.06 mmol) in dichloromethane (30 ml) was left at room temperature for 1 day. The solution was then diluted with dichloromethane (50 ml), the solution shaken with saturated Na₂SO₃ aq. (3×10 ml) and subsequently with saturated NaHCO₃ aq. (2×10 ml) and the dried (MgSO₄) solution evaporated and the solid residue recrystallized from EtOH: yield 60%, m.p. 144°–146° C. ¹H NMR (CDCl₃): δ7.71 and 7.88 (H-3¹, H-4¹), 8.85 (H-4, H-6).

EXAMPLE 80

2-[N-(2-Tolyl)carbamoylmethyl)sulfonyl-4,6-dimethyl-5-bromopyrimidine

A solution of 2-[N-(2-tolyl)carbamoylmethyl)thio-4,6-dimethyl-5-bromopyrimidine (35 mmol) and 85% m-chloroperbenzoic acid (10.5 mmol) in dichloromethane (120 ml) was left at room temperature for 3 days. The mixture was then shaken with saturated Na₂SO₃ aq (3×15 ml) and subsequently with saturated NaHCO₃ aq (2×10 ml) and the dried solution evaporated; yield 85%, m.p. 144° C. ¹H NMR (CDCl₃): δ2.23 (2'-Me), 2.7 (Me₂), 4.53 (CH₂).

EXAMPLE 81

2-Phenylsulfonyl-5-fluoropyrimidine

2-Phenylthio-5-fluoropyrimidine (4 mmol) was dissolved in acetic acid (5 ml), 30% H₂O₂ (0.5 ml) added and the resultant solution stirred at room temperature for 3 days. The product was precipitated by addition of ice cold water (35 ml); yield 71%, m.p. 105° C. (iPrOH). ¹H NMR (CDCl₃): δ7.5–8.1 (Ph), 8.65 (H-4, H-6).

EXAMPLE 82

2-(2-Thienylmethoxycarbonylmethyl)sulfonyl-4,6-dimethyl-5-bromopyrimidine

A solution of 2-(2-thienylmethoxycarbonylmethylthio-4,6-dimethyl-5-bromopyrimidine (4.8 mmol) and 85% m-chloroperbenzoic acid (14.4 mmol) in dichloromethane (100 ml) was left at room temperature for 2 days, more dichloromethane (50 ml) added, the solution shaken with saturated Na₂SO₃ aq (3×20 ml), and with saturated NaHCO₃ (2×10 ml), and the dried (MgSO₄) solution evaporated; yield 44%, m.p. 87°–88° C. (EtOAc/Et₂O). ¹H NMR (CDCl₃): δ2.65 (Me), 4.56 (SO₂CH₂), 5.20 (OCH₂), 6.90/6.93, 7.25 (thiophene).

PHARMACEUTICAL COMPOSITION EXAMPLES

Example A

| Injection solution | |
|---|---|
| 1. Active ingredient | 500 mg |
| 2. Polysorbate 80 | 1.25 mg |
| 3. Sodium chloride | 20 mg |
| 4. Water for injection | to 2.5 ml |

The sterile active ingredient, comminuted as a very fine powder, is dispersed aseptically in an aqueous vehicle containing the wetting agent (Polysorbate 80) and sufficient sodium chloride to produce an approximately isotonic solution, thus providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient with a sterile ampoule of the remaining ingredients to permit extemporaneous preparation of the suspension immediately before injection.

Example B

| Injection solution | |
|---|---|
| 1. Active ingredient | 100 mg |
| 2. Aluminium monostearate | 5 mg |
| 3. Fractionated coconut oil | to 1 ml |

Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intramuscular injection. The dose administered may be adjusted by alteration of the dose volume. The product may be presented in multidose vials, sealed with oil resistant rubber plugs to permit withdrawal of the required dose volume.

Example C

| Tablets | |
|---|---|
| 1. Active ingredient | 250 mg |
| 2. Lactose | 100 mg |
| 3. Maize starch | 20 mg |
| 4. Polyvinyl pyrrolidone | 5 mg |
| 5. Magnesium stearate | 5 mg |

Ingredients 1., 2. and 3. may be blended, mixed to a crumbly consistency with an alcoholic solution of 4, dried at atmospheric pressure, the resulting granules passed through a 20 mesh wire sieve, and the resulting product blended with 5 and compressed into tablets using suitable punches and dies in a tablet compression machine. The tablets may have a thin film coat of, for example hydroxypropyl methyl cellulose applied to them to mask any unpleasant taste.

We claim:

1. A pharmaceutical composition for combating abnormal cell proliferation comprising as active ingredient an effective amount of a compound of the formula:

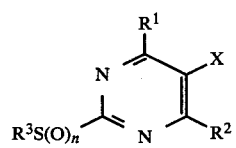

wherein X represents a halogen atom; n is 0, 1 or 2; R¹ and R², which may be the same or different, each represents a hydrogen atom or a C₁₋₄ alkyl group, an amido group, a mono- or di-C₁₋₄ alkylamido group, a carboxyl group or a group of the formula —COORᵃ in which Rᵃ represents a C₁₋₈ alkyl, $C_{2-8}$ alkenyl or $C_{2-8}$ alkynyl group, a $C_{3-8}$ cycloalkyl or $C_{3-8}$ cycloalkenyl group, an aralkyl, aralkenyl or aralkynyl group with up to 4 carbon atoms in the aliphatic moiety, which moiety may be saturated or unsaturated, and up to 10 carbon atoms in the aryl moiety or a $C_{6-10}$ aryl group, the aryl moiety or group being optionally substituted by a $C_{1-4}$ alkyl group; and $R^3$ represents a $C_{1-8}$ alkyl, $C_{2-8}$ alkenyl or $C_{2-8}$ alkynyl group, a $C_{3-8}$ cycloalkyl group, a $C_{3-8}$ cycloalkenyl group, the group Het, wherein Het is a 3–7 membered heterocyclic ring having one or two heteroatoms selected from oxygen, nitrogen or sulphur and optionally carrying one or more $C_{1-4}$ alkyl or $C_{6-10}$ aryl groups; a Het substituted $C_{1-8}$ alkyl, $C_{2-8}$ alkenyl or $C_{2-8}$ alkynyl group, an aralkyl, aralkenyl or aralkynyl group with up to 4 carbon atoms in the aliphatic moiety which moiety may be saturated or unsaturated and up to 10 carbon atoms in the aryl moiety or a $C_{6-10}$ aryl group, the aryl moiety or group being optionally substituted by a $C_{1-4}$ alkyl group, said moieties or groups being optionally substituted by one or more substituents selected from halogen atoms and oxo, nitro, hydroxy, mercapto, Het as herein defined, $-OR^b$, $-COOR^b$, $-SR^b$, $R^bSO-$, $R^bSO_2-$, wherein $R^b$ is as defined for $R^a$ or Het and is optionally substituted by one or more substituents selected from halogen, oxo, amino, hydroxy, mercapto, Het as herein defined, $-OR^a$, $-COOR^a$, $-SR^a$, $R^aSO-$, or $R^aSO_2-$; $C_{1-8}$ alkanoylamino, di($C_{1-8}$ alkyl)-phosphonate and amino groups of the formula

in which $R^c$ and $R^d$, which may be the same or different, each represents a hydrogen atom or a $C_{1-4}$ alkyl, $C_{6-10}$ aralkyl or $C_{6-10}$ aryl group, the aryl moiety or group being optionally substituted by a $C_{1-4}$ alkyl group or $R^c$ and $R^d$ together with the nitrogen atom therebetween represents a perhydroazocinyl group; with the proviso that $R^3$ is other than a 1-alkyl-5-nitro-imidazolyl-2-alkyl grop when n is 0 or, where an acidic or basic group is present, a physiologically compatible salt thereof in association with a pharmaceutical carrier or excipient.

2. The composition of claim 1, wherein $R_3$ represents a group Het', wherein Het' is a 3–7 membered heterocyclic ring having one or two heteroatoms selected from oxygen, nitrogen or sulphur, optionally carrying one or two substituents selected from halogen atoms, oxo or nitro groups; a $C_{1-4}$ alkyl group optionally carrying halogen, Het', Het'O—, $C_{6-10}$ aryloxy, halosubstituted $C_{6-10}$ aryloxy or di($C_{1-4}$ alkyl) phosphonate; a $C_{2-4}$ alkenyl group optionally carrying oxo, Het' or $C_{6-10}$ aryl; a $C_{6-10}$ aryl group optionally carrying a $C_{1-4}$ alkyl substituent; or an aralkyl group with up to four carbon atoms in the alkyl moiety and up to ten carbon atoms in the aryl moiety.

3. The composition of claim 1, wherein $R_3$ is a $C_{1-4}$ alkyl group optionally carrying halogen, a $C_{2-4}$ alkenyl group optionally carrying oxo or phenyl, a phenyl group optionally carrying a $C_{1-4}$ alkyl group, a benzyl group or a methyl group carrying Het", -O-Het" or phenoxy optionally substituted by chlorine; wherein Het" is a 5- or 6-membered heterocyclic ring having one or two hetero atoms selected from oxygen, nitrogen or sulphur optionally carrying one or two substituents selected from chlorine atoms or oxo groups.

4. The composition of claim 1, wherein $R_3$ is a $C_{1-4}$ alkyl group optionally carrying iodine or chlorine, a $C_{2-4}$ alkenyl group substituted by an oxo or phenyl group, a phenyl group, tolyl group, a benzyl group or a methyl group carrying Het" or —O—Het", wherein Het" is a 5- or 6-membered heterocyclic ring having one or two hetero atoms selected from oxygen, nitrogen or sulphur optionally carrying one or two substituents selected from chlorine atoms or oxo groups.

5. The composition of claim 2, wherein $R^1$ and $R^2$ are the same or different and are hydrogen or methyl and n is 2.

6. The composition of claim 3, wherein $R^1$ and $R^2$ are the same or different and are hydrogen or methyl and n is 2.

7. The composition of claim 4, wherein $R^1$ and $R^2$ are the same or different and are hydrogen or methyl and n is 2.

8. A composition as claimed in claim 1 which comprises as active ingredient a compound of formula I wherein $R^1$ and $R^2$ each represent a hydrogen atom.

9. A composition as claimed in claim 1 which comprises as active ingredient a compound of formula I wherein n is 2.

10. A composition as claimed in claim 1 which comprises as active ingredient:
2-methylsulfonyl-5-chloropyrimidine,
2-(chloromethyl)sulfonyl-5-chloropyrimidine,
2-styrylsulfonyl-5-chloropyrimidine,
2-benzylsulfonyl-5-chloropyrimidine,
2-(3-Oxobuten-1-yl)sulfonyl-5-chloropyrimidine,
2-(iodomethyl)sulfonyl-5-chloropyrimidine,
2-benzylsulfonyl-5-bromopyrimidine,
2-(5-chloropyrimidine-2-oxymethyl)sulfonyl-5-chloropyrimidine or
2-benzylsulfinyl-5-chloropyrimidine.

11. A composition as claimed in claim 1 wherein $R^a$ is $C_{1-4}$ alkyl.

12. A composition as claimed in claim 1 wherein $R^3$ is methyl, chloromethyl, iodomethyl, acetyl substituted methyl, ethyl, or vinyl; phenyl, thienyl or a methyl group substituted with a 5-halopyrimidin-2-oxy group and $R^1$ and $R^2$ are hydrogen.

13. A compound which is:
2-(chloromethyl)sulfonyl-5-chloropyrimidine,
2-(3-oxobuten-1-yl)sulfonyl-5-chloropyrimidine,
3-(iodomethyl)sulfonyl-5-chloropyrimidine or
2-(5-chloropyrimidine-2-oxymethyl)sulfonyl-5-chloropyrimidine.

* * * * *